United States Patent
Butler

(10) Patent No.: US 11,291,422 B2
(45) Date of Patent: Apr. 5, 2022

(54) RECONSTRUCTING CARDIAC FREQUENCY PHENOMENA IN ANGIOGRAPHIC DATA

(71) Applicant: William E. Butler, Boston, MA (US)

(72) Inventor: William E. Butler, Boston, MA (US)

(*) Notice: Subject to any disclaimer, the term of this patent is extended or adjusted under 35 U.S.C. 154(b) by 0 days.

(21) Appl. No.: 16/832,695

(22) Filed: Mar. 27, 2020

(65) Prior Publication Data

US 2020/0305822 A1    Oct. 1, 2020

Related U.S. Application Data

(60) Provisional application No. 62/824,582, filed on Mar. 27, 2019.

(51) Int. Cl.
*A61B 6/00* (2006.01)
*G06T 11/00* (2006.01)

(52) U.S. Cl.
CPC ............ *A61B 6/504* (2013.01); *A61B 6/5217* (2013.01); *A61B 6/5288* (2013.01); *G06T 11/006* (2013.01); *G06T 2211/404* (2013.01)

(58) Field of Classification Search
None
See application file for complete search history.

(56) References Cited

U.S. PATENT DOCUMENTS

| | | | |
|---|---|---|---|
| 3,335,716 A | 8/1967 | Alt et al. | |
| 5,637,871 A | 6/1997 | Piety et al. | |
| 5,963,676 A | 10/1999 | Wu et al. | |
| 6,195,456 B1 | 2/2001 | Balasubramanian et al. | |
| 6,442,414 B1 | 8/2002 | Watanabe | |
| 6,549,801 B1 | 4/2003 | Chen et al. | |
| 6,842,638 B1 | 1/2005 | Suri et al. | |
| 6,975,753 B2 | 12/2005 | Matsuura et al. | |
| 6,985,632 B2 | 1/2006 | Sato et al. | |
| 7,020,314 B1 | 3/2006 | Suri et al. | |
| 7,035,679 B2 | 4/2006 | Addison et al. | |
| 7,201,892 B2 | 4/2007 | Achilefu et al. | |
| 7,359,062 B2 | 4/2008 | Chen et al. | |
| 7,602,183 B2 | 10/2009 | Lustig et al. | |

(Continued)

FOREIGN PATENT DOCUMENTS

| CN | 101406392 B | 5/2011 |
|---|---|---|
| EP | 1322219 B1 | 5/2007 |

(Continued)

OTHER PUBLICATIONS

Co-Pending U.S. Appl. No. 16/784,125, filed Feb. 6, 2020 (63 pages).

(Continued)

*Primary Examiner* — Hoon K Song
(74) *Attorney, Agent, or Firm* — Edell, Shapiro & Finnan, LLC

(57) ABSTRACT

Techniques are provided for reconstructing cardiac frequency phenomena from a sequence of angiographic images, i.e., two-dimensional projection images acquired at faster than cardiac rate (greater than two-fold), and analyzed to provide a spatiotemporal reconstruction of moving vascular pulse waves according to that projection. In aspects, a cardiac frequency bandpass filter and/or a Eulerian magnification may be applied to the angiographic data to output the spatiotemporal reconstruction of cardiac frequency angiographic phenomena.

25 Claims, 11 Drawing Sheets

(56) References Cited

U.S. PATENT DOCUMENTS

| | | |
|---|---|---|
| 8,244,334 B2 | 8/2012 | Huang et al. |
| 8,306,295 B2 | 11/2012 | Bruder et al. |
| 8,306,303 B2 | 11/2012 | Bruder et al. |
| 8,417,048 B2 | 4/2013 | Reboni et al. |
| 8,559,692 B2 | 10/2013 | Reboni et al. |
| 8,605,976 B2 | 12/2013 | Diamant et al. |
| 8,611,633 B2 | 12/2013 | Kwon et al. |
| 8,628,751 B2 | 1/2014 | Neumann et al. |
| 8,948,480 B2 | 2/2015 | Liu et al. |
| 9,019,305 B2 | 4/2015 | Baumgart et al. |
| 9,036,780 B2 | 5/2015 | Kyriakou et al. |
| 9,165,349 B2 | 10/2015 | Kwon et al. |
| 9,324,005 B2 | 4/2016 | Wadhwa et al. |
| 9,345,413 B2 | 5/2016 | Schie et al. |
| 9,357,916 B2 | 6/2016 | Srivastava et al. |
| 9,811,901 B2 | 11/2017 | Wu et al. |
| 9,814,384 B2 | 11/2017 | Schmoll |
| 9,836,849 B2 | 12/2017 | Dickrell, III et al. |
| 10,123,761 B2 | 11/2018 | Butler |
| 10,226,176 B2 | 3/2019 | Schmoll |
| 10,299,677 B2 | 5/2019 | Spaide |
| 10,653,379 B2 | 5/2020 | Rapoport |
| 2004/0101090 A1 | 5/2004 | Drummond et al. |
| 2005/0080327 A1 | 4/2005 | Jenkins et al. |
| 2007/0106146 A1 | 5/2007 | Altmann et al. |
| 2007/0106149 A1 | 5/2007 | Mistretta |
| 2007/0185393 A1 | 8/2007 | Zhou et al. |
| 2008/0045847 A1 | 2/2008 | Farag et al. |
| 2008/0226149 A1 | 9/2008 | Wischmann et al. |
| 2010/0113949 A1 | 5/2010 | Sathyanarayana |
| 2011/0142288 A1 | 6/2011 | Diamant et al. |
| 2012/0134553 A1 | 5/2012 | Liao et al. |
| 2013/0101187 A1* | 4/2013 | Sundar ............... G06T 7/246 382/128 |
| 2013/0116554 A1 | 5/2013 | Kaiser et al. |
| 2013/0243348 A1 | 9/2013 | Goshen et al. |
| 2014/0005563 A1 | 1/2014 | Ramanathan et al. |
| 2014/0044330 A1* | 2/2014 | Klingenbeck ........ A61B 6/5217 382/130 |
| 2014/0072190 A1 | 3/2014 | Wu et al. |
| 2014/0072228 A1 | 3/2014 | Rubinstein et al. |
| 2014/0072229 A1 | 3/2014 | Wadhwa et al. |
| 2014/0378795 A1 | 12/2014 | McKenna |
| 2015/0045684 A1 | 2/2015 | Schie |
| 2015/0190533 A1 | 7/2015 | Newton et al. |
| 2015/0257653 A1 | 9/2015 | Hyde et al. |
| 2016/0135775 A1 | 5/2016 | Mistretta et al. |
| 2016/0189394 A1 | 6/2016 | Zhang et al. |
| 2016/0220112 A1 | 8/2016 | Schmoll |
| 2016/0267704 A1 | 9/2016 | Mistretta et al. |
| 2016/0349346 A1 | 12/2016 | Cheng |
| 2017/0000441 A1 | 1/2017 | Butler |
| 2017/0367603 A1 | 12/2017 | Spector |
| 2018/0047160 A1 | 2/2018 | Wu et al. |
| 2018/0055471 A1 | 3/2018 | Redel |
| 2019/0015061 A1* | 1/2019 | Liebeskind ........... G06T 7/0012 |
| 2019/0046147 A1 | 2/2019 | Butler |
| 2019/0053780 A1 | 2/2019 | Song et al. |
| 2019/0159707 A1 | 5/2019 | Albuquerque et al. |
| 2019/0343383 A1 | 11/2019 | Spaide |
| 2020/0193597 A1 | 6/2020 | Fan et al. |
| 2020/0245961 A1 | 8/2020 | Butler |
| 2020/0245965 A1 | 8/2020 | Butler |
| 2020/0286237 A1 | 9/2020 | Butler |
| 2020/0305822 A1 | 10/2020 | Butler |
| 2020/0320710 A1 | 10/2020 | Butler |
| 2020/0397396 A1 | 12/2020 | Butler |
| 2021/0137634 A1 | 5/2021 | Lang |

FOREIGN PATENT DOCUMENTS

| | | |
|---|---|---|
| WO | 2020163614 A1 | 8/2020 |
| WO | 2020163629 A1 | 8/2020 |
| WO | 2020185706 A1 | 9/2020 |
| WO | 2020198592 A1 | 10/2020 |
| WO | 2020206430 A1 | 10/2020 |

OTHER PUBLICATIONS

YouTube video, "Eulerian Video Magnification" accessed online on Jun. 15, 2020 at: <https://www.youtube.com/watch?v=ONZcjs1Pjmk>, published May 23, 2012 (2 pages).

International Search Report and Written Opinion received in international application No. PCT/US2020/025229, dated Jun. 16, 2020 (17 pages).

Wikipedia article entitled "Band-pass filter", <https://en.wikipedia.org/wiki/Band-pass_filter>, last edited on Feb. 25, 2020, accessed on Mar. 26, 2020 (4 pages).

Sarode, L., & N. Mandaogade, N, "Video Motion Magnification using Spatio-Temporal Algorithm," International Journal of Computer Applications, 96(9), p. 9-13, 2014, (5 pages).

Shenoi, Belle A, "Introduction to digital signal processing and filter design," John Wiley and Sons, Chapter 3, 2006, (91 pages).

Martin J. Murphy, "Tracking Moving Organs in Real Time", Seminars in Radiation Oncology, vol. 14, No. 1, Jan. 2004, pp. 91-100.

Medda et al., A wavelet clustering technique for the identification of functionally connected regions in the rat brain using resting state fMRI, IEEE Statistical Signal Processing Workshop (SSP), Aug. 2012, pp. 424-427.

Mizuno-Matsumoto et al., Wavelet-crosscorrelation analysis: Nonstationary analysis of neurophysiological signals, Brain Topography, 2005, vol. 17, No. 4, pp. 237-252.

Morlet et al., Wave propagation and sampling theory-part I: Complex signal and scattering in multilayered media, Seophysics, Feb. 1982, vol. 47, No. 2, pp. 203-221.

Najmi et al., The continuous wavelet transform and variable resolution time-frequency analysis, Johns Hopkins Apl Technical Digest, 1997, vol. 18, No. 1, pp. 134-140.

Schultze-Kraft et al., Exploiting the potential of three dimensional spatial wavelet analysis to explore nesting of temporal oscillations and spatial variance in simulateous EEG-fMRI data, Progress in Biophysics and Molecular Biology, Mar. 2011, vol. 105(1-2), pp. 67-79.

Serroukh, Wavelet coefficients cross-correlation analysis of times series, Electronic Journal of Applied Statistical Analysis, 2012, vol. 5, iss. 2, pp. 289-296.

Shannon, Communication in the Presence of Noise, Proceedings of the IEEE, Feb. 1998, vol. 86, iss. 2, pp. 447-457.

Hardesty et al., Safety, efficacy, and cost of intraoperative indocyanine green angiography compared to intraoperative catheter angiography in cerebral aneurysm surgery, Journal of clinical neuroscience, Apr. 2014, pp. 1-6.

Hyvarinen et al., Indocyanine green fluorescence angiography, Acta Ophthalmologica, Aug. 1980, vol. 58(4), pp. 528-538.

Aaslid et al., Noninvasive transcranial doppler ultrasound recording of flow velocity in basal cerebral arteries, J Neurosurg, 1982, vol. 57(6), pp. 769-774.

Vo et al., Vonn distribution of relative phase for statistical image modeling in complex wavelet domain, Signal Processing, 2011, vol. 91(1), pp. 114-125.

Abramovich et al., Wavelet Analysis and Its Statistical Applications, Journal of the Royal Statistical Society Series D (The Statistician), 2000, vol. 49(1), pp. 1-29.

Kim et al., Cine MR CSF flow study in hydrocephalus: what are the valuable parameters? Acta neurochirurgica Supplement, 1998, vol. 71(6), pp. 343-346.

Kulkarni et al., Endoscopic third ventriculostomy in the treatment of childhood hydrocephalus, The Journal of Pediatrics, Aug. 2009, vol. 155, No. 2, pp. 254-259.

Meairs et al., Ultrasound, microbubbles and the blood-brain barrier, Progress in Biophysics & Molecular Biology, Apr. 2007, vol. 93(1-3), pp. 354-362.

Saikali et al., A three-dimensional digital segmented and deformable brain atlas of the domestic pig, Journal of Neuroscience Methods, Sep. 2010, vol. 192(1), pp. 102-109.

(56) References Cited

OTHER PUBLICATIONS

Wilson, Monro-Kellie 2.0: The dynamic vascular and venous pathophysiological components of intracranial pressure, Journal of Cerebral Blood Flow & Metabolism, May 2016, vol. 36(8), pp. 1338-1350.
Bernstein et al., Handbook of MRI Pulse Sequences, Elsevier Academic Press, 2004, pp. 443-454.
Kim et al., Phase-shift between arterial flow and ICP pulse during infusion test, Acta Neurochirurgica, Feb. 3, 2015, vol. 157(4), pp. 633-638.
Kawoos et al., Advances in Intracranial Pressure Monitoring and Its Significance in Managing Traumatic Brain Injury, International Journal of Molecular Sciences, 2015, vol. 16 (12), pp. 28979-28997.
Gabor, Theory of communication. Part 2: The analysis of hearing, Journal of the Institution of Electrical Engineers—Part III: Radio and Communication Engineering, 1946, vol. 93(26), pp. 442-445.
Goriely et al., Mechanics of the brain: perspectives, challenges, and opportunities, Biomechanics and modeling in mechanobiology, Feb. 26, 2015, vol. 14(5), pp. 931-965.
Helbok et al., Intracranial Pressure and Cerebral Perfusion Pressure Monitoring in Non-TBI Patients: Special Considerations, Neurocritical Care, 2014, vol. 21 (S2), pp. S85-94 (published online, Sep. 11, 2014, 10 pages).
Balestreri et al., Intracranial hypertension: what additional information can be derived from ICP waveform after head injury?, Acta Neurochirurgica (wien), 2004, vol. 146(2), pp. 131-141.
Carrera et al., What Shapes Pulse Amplitude of Intracranial Pressure?, Journal of Neurotrauma, Feb. 2010, vol. 27(2), pp. 317-324.
Bangare et al., Reviewing Otsu's method for image thresholding, International Journal of Applied Engineering Research, 2015, vol. 10, No. 9, pp. 21777-21783.
Bhadelia et al., Analysis of cerebrospinal fluid flow waveforms with gated phase-contrast MR velocity measurements, American Journal of Neuroradiology, Feb. 1995, vol. 16(2), pp. 389-400.
Bonnefous et al., Quantification of arterial flow using digital subtraction angiography, Medical Physics, Oct. 2012, vol. 39, iss. 10, pp. 6264 6275.
Chang et al., Emerging techniques for evaluation of the hemodynamics of intracranial vascular pathology, The Neuroradiology Journal, Feb. 2015, vol. 28(1), pp. 19-27.
Dawkins et al., Complications of cerebral angiography: A prospective analysis of 2,924 consecutive procedures, Neuroradiology, Aug. 2007, vol. 49, iss. 9, pp. 753-759.
Torrence et al., A Practical Guide to Wavelet Analysis, Bulletin of the American Meteorological Society, Jan. 1998, vol. 79, iss. 1, pp. 61-78.
Zou et al., Increased Phase Synchronization between Intracranial Pressure and Arterial Blood Pressure during Elevated Intracranial Pressure in Dogs, Proceedings of the 2005 IEEE, Engineering in Medicine and Biology 27th Annual Conference, Shanghai, China, Sep. 1-4, 2005, pp. 315-318.
Unekawa et al., RBC velocities in single capillaries of mouse and rat brains are the same, despite 10-fold difference in body size, Brain Research, 2010, vol. 1320, pp. 69-73.
Grinsted et al., Application of the cross wavelet transform and wavelet coherence to geophysical time series, Nonlinear Processes in Geophysics, 2004, vol. 11, pp. 561-566.
Grist et al., Time-Resolved Angiography: Past, Present, and Future, Journal of Magnetic Resonance Imaging, 2012, vol. 36(6), pp. 1273-1286.
Jiang et al., Computational Fluid Dynamics Simulations of Intracranial Aneurysms at Varying Heart Rates: A "Patient-Specific" Study, Journal of Biomechanical Engineering, Sep. 2009, vol. 131(9), pp. 09100-1-09100-11.
Kachelriess et al., ECG-correlated image reconstruction from subsecond multi-slice spiral CT scans of the heart, Medical Physics, 2000, vol. 27(12), pp. 1881-1902.
Kirk et al., Phase-only complex-valued spatial filter, Journal of the Optical Society of America, Aug. 1971, vol. 61, Iss. 8, pp. 1023-1028.
Latka et al., Phase dynamics in cerebral autoregulation, American journal of physiology, heart and circulatory physiology, 2005, vol. 289(5), pp. H2272-H2279.
Shpilfoygel et al., X-ray videodensitometric methods for blood flow and velocity measurement: A critical review of literature, Medical Physics, Sep. 2000, vol. 27, iss. 9, pp. 2008-2023.
Mistretta, Sub-Nyquist acquisition and constrained reconstruction in time resolved angiography, Medical Physics, 2011, vol. 38, iss. 6, pp. 2975-2985.
Peng et al., Wavelet phase synchronization analysis of cerebral blood flow autoregulation, IEEE Transactions on Biomedical Engineering, Apr. 2010, vol. 57, No. 4, pp. 960-968.
Pereira et al., A DSA-based method using contrast motion estimation for the assessment of the intra-aneurysmal flow changes induced by flow-diverter stents, American Journal of Neuroradiology, Apr. 2013, vol. 34(4), pp. 808-815.
Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (8 pages).
Ashmead, John, "Morlet Wavelets in Quantum Mechanics," Quanta, vol. 1, issue 1, Nov. 2012, pp. 58-70 (13 pages).
Baker et al., "Lucas-Kanade 20 Years On: A Unifying Framework," International Journal of Computer Vision 56(3), 221-255, 2004 (35 pages).
Balakrishnan et al., "VoxelMorph: A Learning Framework for Deformable Medical Image Registration," arXiv:1809.05231 [cs.CV], Sep. 1, 2019 (16 pages).
Bao et al., "Depth-Aware Video Frame Interpolation," IEEE Conference on Computer Vision and Pattern Recognition, pp. 3703-3712, 2019 (10 pages).
Butler, William E., "Wavelet brain angiography suggests arteriovenous pulse wave phase locking," Plos One, Nov. 15, 2017 (23 pages).
Chen et al., "A Labeling-Free Approach to Supervising Deep Neural Networks for Retinal Blood Vessel Segmentation," Chongqing University, China, May 1, 2017 (10 pages).
Bao et al., https://github.com/baowenbo/DAIN, "DAIN (Depth-Aware Video Frame Interpolation)", IEEE Conference on Computer Vision and Pattern Recognition, Long Beach, CVPR 2019 (9 pages).
Dalca et al., "Unsupervised Learning of Probabilistic Diffeomorphic Registration for Images and Surfaces," Jul. 23, 2019 (18 pages).
Garyfallidis et al., "Dipy, a library for the analysis of diffusion MRI data," Frontiers in Neuroinformatics, vol. 8, art. 8, Feb. 21, 2014 (17 pages).
DIPY—Diffusion Imaging In Python; https://dipy.org/; accessed Mar. 1, 2021 (8 pages).
Daubechies, Ingrid, "Ten Lectures on Wavelets," CBMS-NSF Regional Conference Series in Applied Mathematics, Sep. 1992 (342 pages).
Farneback, Gunnar, "Very High Accuracy Velocity Estimation using Orientation Tensors, Parametric Motion, and Simultaneous Segmentation of the Motion Field," Proceedings Eighth IEEE International Conference on Computer Vision, Jul. 2001 (7 pages).
Felsberg and Sommer, "The monogenic signal," IEEE Transactions on Signal Processing, (49), 12, 3136-3144, 2001 (10 pages).
Chapter 2: Multiscale Vessel Enhancement Filtering, pp. 7-16, adapted from: Frangi et al., "Multiscale Vessel Enhancement Filtering," Medical Image Computing and Computer-Assisted Intervention—MICCAI'98, Lecture Notes in Computer Science, vol. 1496, Springer Verlag, Berlin, Germany, pp. 130-137, 1998 (10 pages).
Freeman and Adelson," The Design and Use of Steerable Filters," IEEE Transactions on Pattern Analysis and Machine Intelligence, vol. 13, No. 9, pp. 891-906, Sep. 1991 (16 pages).
Gabor, D., "Theory of Communication," Sep. 24, 1945 (29 pages).
Goupillaud et al., "Cycle-Octave and Related Transforms in Seismic Signal Analysis," Geoexploration, 23, (1984/85), pp. 85-102 (18 pages).
Harris and Stephens, "A Combined Corner and Edge Detector," Alvey Vision Conference, pp. 147-151, 1988 (5 pages).
Horn and Schunck, "Determining Optical Flow," Artificial Intelligence 17, pp. 185-203, 1981 (19 pages).

(56) References Cited

OTHER PUBLICATIONS

Wolfram Research, "ImageDisplacements," Wolfram Language function, https://reference.wolfram.com/language/ref/ImageDisplacements.html, 2016 (5 pages).
Lucas and Kanade, "An Iterative Image Registration Technique with an Application to Stereo Vision," Proceedings DARPA Image Understanding Workshop, Apr. 1981, pp. 121-130 (10 pages).
Morlet et al., "Wave propogation and sampling theory—Part I: Complex signal and scattering in multilayered media," Geophysics, vol. 47, No. 2, Feb. 1982, pp. 203-221 (19 pages).
Shi and Tomasi, "Good Features to Track," IEEE Conference on Computer Vision and Pattern Recognition, Seattle, Jun. 1994 (8 pages).
Simoncelli and Farid, "Steerable Wedge Filters for Local Orientation Analysis," IEEE Transactions on Image Processing, 5(9): 1377-1382, 1996 (10 pages).
Unser and Van De Ville, "Wavelet Steerability and the Higher-Order Riesz Transform," IEEE Transactions On Image Processing, vol. 19, No. 3, Dec. 22, 2009 (17 pages).
Yin et al., "Reducing the X-ray radiation exposure frequency in cardio-angiography via deep-learning based video interpolation," Jun. 1, 2020 (6 pages).
Bracewell, R.N., "Two-Dimensional Imaging", Prentice Hall, chapters 4-7, 12, and 15, 1995 (pp. 1-100 of 206 pages).
Bracewell, R.N., "Two-Dimensional Imaging", Prentice Hall, chapters 4-7, 12, and 15, 1995 (pp. 101-206 of 206 pages).
Des Plantes, "Eine Neue Methode Zur Differenzierung in der Rontgenographie (Planigraphies)," Acta Radiologica, 13:2, 182-192, 1932 (16 pages).
Tuy, H. K., "An Inversion Formula for Cone-Beam Reconstruction," SIAM Journal on Applied Mathematics, 43(3):546-552, 1983 (7 pages).
Nyqvist, H., "Certain Topics in Telegraph Transmission Theory," Transactions of the AIEE, vol. 47, pp. 617-644, 1928 (28 pages).
Kotelnikov, V.A., "On the transmission capacity of the 'ether' and of cables in electrical communications," Proceedings of the first All-Union Conference on the technological reconstruction of the communications sector and the development of low-current engineering, Moscow, 1933 (23 pages).
Shannon, C.E., "Communication in the Presence of Noise," Proceedings of the Institute of Radio Engineers, vol. 37, No. 1, pp. 10-21, 1949 (11 pages).
Butler, W.E., "Wavelet brain angiography suggests arteriovenous pulse wave phase locking," PLOS ONE, Nov. 15, 2017 (16 pages).
Sagel, S.S., "Gated Computed Tomography of the Human Heart," Investigative Radiology, vol. 12, No. 6, pp. 563-566, 1977 (4 pages).
Wikipedia article "Dose Area Product" accessed online on Jun. 15, 2020 at: <https://en.wikipedia.org/wiki/Dose_area_product> (2 pages).
Zhao et al., Ultrasound Contrast Imaging Based on a Novel Algorithm Combined Pulse Inversion with Wavelet Transform, Ultrasound in Medicine & Biology, 2011, vol. 37, No. 8, pp. 1292-1305.
Faubel et al., Cilia-based flow network in the brain ventricles, Neurophysiology, Jul. 8, 2016, vol. 353, iss. 6295, pp. 176-178.
Marshall et al., Cilia orientation and the fluid mechanics of development, Current Opinion in Cell Biology, 2008, vol. 20(1), pp. 48-52.
Ohata et al., Mechanosensory Genes Pkd1 and Pkd2 Contribute to the Planar Polarization of Brain Ventricular Epithelium, The Journal of Neuroscience, Aug. 5, 2015, vol. 35(31), pp. 11153-11168.
Jalalvand et al., Ciliated neurons lining the central canal sense both fluid movement and pH through ASIC3, Nature Communications, Jan. 8, 2016, pp. 1-12.
Wagshul et al., Resonant and notch behavior in intracranial pressure dynamics, J Neurosurgery Pediatrics, May 2009, vol. 3(5), pp. 354-364.
Park et al., Alterations of pulsation absorber characteristics in experimental hydrocephalus, J Neurosurg Pediatrics, Aug. 2010, vol. 6(2), pp. 159-170.
Kotelnikov, On the transmission capacity of the "ether" and of cables in electrical communication, Proceedings of the first All-Union Conference on the technological reconstruction of the communications sector and low-current engineering, Moscow 1933, vol. 1, pp. 1-23.
Sagel et al., Gated computed tomography of the human heart, Investigative radiology, Nov.-Dec. 1977, vol. 12, iss. 6, pp. 563-566.
Sarode et al., Video Motion Magnification Using Spatio-Temporal Algorithm, International Journal of Computer Applications (0975-8887), Jun. 2014, vol. 96, No. 9, pp. 9-13.
Zhao et al., Phase-Resolved Optical Coherence Tomography and Optical Doppler Tomography for Imaging Blood Flow in Human Skin with Fast Scanning Speed and High Velocity Sensitivity, Optics Letters, Jan. 15, 2000, vol. 25, Iss. 2, pp. 114-116.
Yazdanfar et al., High Resolution Imaging of In vivo Cardiac Dynamics Using color Doppler Optical Coherence Tomography, Optics Express, Dec. 22, 1997, vol. 1, No. 13, pp. 424-431.
Wu et al., Eulerian Video Magnification for Revealing Subtle Changes in the World, ACM Transactions on Graphics, Jul. 1, 2012, vol. 31, iss. 4, pp. 1-8.
Wang et al., Phase-Sensitive Optical Coherence Elastography for Mapping Tissue Microstains in Real Time, Applied Physics Letter, 2007, vol. 90, pp. 164105-1-164105-3.
Robles et al., Assessing Hempglobin Concentration Using Spectroscopic Optical Coherence Tomography for Feasibility of Tissue Diagnostics, Biomedical Optics Express, Aug. 2, 2010, vol. 1, No. 1, pp. 310-317.
Lahiri et al., Medical Applications of Infrared Thermography: A Review, Infrared Physics & Technology, 2012, vol. 55, pp. 221-235.
Mourant et al., Hemoglobin Parameters from Diffuse Reflectance Data, Journal of Biomedical Optics, Mar. 2014, vol. 19, iss. 3, pp. 037004-1-037004-9.
Makita et al., Optical Coherence Angiography, Optics Express, Aug. 21, 2006, vol. 14, No. 17, pp. 7821-7840.
Chen et al., Noninvasive Imaging of in vivo blood flow velocity using optical Doppler tomography, Optics Letters, Jul. 15, 1997, vol. 22, No. 14, pp. 1119-1121.
Izatt et al., In vivo bidirectional color Doppler flow imaging of picoliter blood volumes using optical coherence tomography, Optics Letters, Sep. 15, 1997, vol. 22, No. 18, pp. 1439 1441.
Drexler, Ultrahigh-Resolution Optical Coherence Tomography, Journal of Biomedical Optics, Jan./Feb. 2004, vol. 9, iss. 1, pp. 47-74.
Devor et al., Frontiers in optical imaging of cerebral blood flow and metabolism, Journal of Cerebral Blood Flow & Metabolism, 2012, vol. 32, pp. 1259-1276.
Chen et al., Optical Doppler Tomography, IEEE Journal on Selected Topics in Quantum Electronics, Jul. 1, 1999, vol. 5, No. 4, pp. 1134-1142.
Bachmann et al., Fluorescence Spectroscopy of Biological Tissues—A Review, Applied Spectroscopy Reviews, 2006, vol. 41, pp. 575-590.
Desmettre et al., Fluorescence Properties and Metabolic Features of Indocyanine Green (ICG) as Related to Angiography, Survey of Ophthalmology, Jul.-Aug. 2000, vol. 45, No. 1, pp. 15-27.
Martin et al., Hydrodynamic and longitudinal impedance analysis of cerebrospinal fluid dynamics at the craniovertebral junction in type I Chiari malformation, PloS One, Oct. 2013, vol. 8, iss. 10, pp. 1-9.
Anonymous, Artis Zeego, Data Sheet VC21, Multi-axis for interventional imaging, Oct. 2014, 36 pages, www.siemens.com/healthcare.
Babin et al. Segmentation and length measurement of the abdominal blood vessels in 3-D MRI images, Conference Proceedings IEEE Engineering in Medicine and Biology Society, Sep. 2-6, 2009, pp. 4399-4402.
Barfett et al., Intra-vascular blood velocity and volumetric flow rate calculated from dynamic 4D CT angiography using a time of flight technique, The International Journal of Cardiovascular Imaging, Oct. 2014, vol. 30(7), pp. 1383-1392.
Bhadelia et al., Cerebrospinal fluid pulsation amplitude and its quantitative relationship to cerebral blood flow pulsations: a phase-contrast MR flow imaging study, Neuroradiology, Apr. 1997, vol. 39(4), pp. 258-264.
Long et al., Spatiotemporal wavelet analysis for functional MRI, NeuroImage, Oct. 2004, vol. 23(2), pp. 500-516.

(56) References Cited

OTHER PUBLICATIONS

Daubechies, The wavelet transform, time-frequency localization, and signal analysis, IEEE Transactions on Information Theory, Sep. 1990, vol. 36, iss. 5, pp. 961-1005.
Gabor, Theory of communication. Part I: The analysis of information, Journal of the Institution of Electrical Engineers—Part III: Radio and Communication Engineering, Nov. 1946, vol. 93(26), pp. 429-441.
Goupillaud et al., Cycle-octave and related transforms in seismic signal analysis, Geoexploration, Oct. 1984, vol. 23, iss. 1, pp. 85-102.
Kuroiwa et al.. Development and clinical application of near-infrared surgical microscope: preliminary report, Minimally invasive neurosurgery: MIN, Dec. 2001, vol. 44(4), pp. 240-242.
Markl et al., 4D Flow MRI, Journal of Magnetic Resonance Imaging (JMRI), Oct. 2012, vol. 36, iss. 5, pp. 1015-1036.
Moser et al., On the accuracy of EPI-based phase contrast velocimetry, Magnetic Resonance Imaging, Nov. 2000, vol. 18, iss. 9, pp. 1115-1123.
Nyquist et al., Certain topics in telegraph transmission theory, Transactions of the American Institute of Electrical Engineers, Feb. 1928, vol. 47, iss. 2, pp. 617-644.
Persson et al., Hydrocephalus prevalence and outcome in a population-based cohort of children born in 1989-1998, Acta Paediatrica, Jun. 2005, vol. 94, iss 6, pp. 726-732.
Provost et al., 3D Ultrafast ultrasound imaging in vivo, Physics in Medicine and Biology, Sep. 10, 2014, vol. 59, iss. 19, L1-L13.
Raabe et al., Prospective evaluation of surgical microscope-integrated intraoperative near-infrared indocyanine green videoangiography during aneuryism surgery, Journal of Neurosurgery, Dec. 2005, vol. 103, iss. 6, pp. 982-989.
Rao et al., Shear strain imaging using shear deformations, Med Phys., Feb. 2008, vol. 35(2), pp. 412-423.
Rasul et al., Is endoscopic third ventriculostomy superior to shunts in patients with non-communicating hydrocephalus? A systematic review and meta-analysis of the evidence, Acta Neurochirurgica, May 2013, vol. 155, iss. 5, pp. 883-889.
Sugawara et al., Arterial path length measurements required for the pulse wave velocity, Journal of Hypertension, May 2009, vol. 27, iss. 5, pp. 1102-1104.
Tomita et al., Automated method for tracking vast numbers of FITC-labeled RBCs in microvessels of rat brain in vivo using a high-speed confocal microscope system, Microcirculation, Feb. 2008, vol. 15, iss. 2, pp. 163-174.
Unser, Sampling- 50 years after Shannon, Proceedings of the IEEE, Apr. 2000, vol. 88, No. 4, pp. 569-587.
Wagshul et al., The pulsating brain: A review of experimental and clinical studies of intracranial pulsatility. Fluids anti Barriers of the CNS, Jan. 18, 2011, vol. 8, iss 5, pp. 1-23.
Weaver et al., Brain mechanical property measurement using MRE with intrinsic activation, Physics in Medicine Biology, Nov. 2012, vol. 57, No. 22, pp. 7275-7287.
Zaidi et al., Indocyanine Green Angiography in the Surgical Management of Cerebral Arteriovenous Malformations Lessons Learned in 130 Consecutive Cases, Operative Neurosurgery, Jun. 2014, vol. 10, No. 2, pp. 246-251.
Zou et al., Intracranial pressure waves: characterization of a pulsation absorber with notch filter properties using systems analysis, J. Neurosurg Pediatrics, Jul. 2008, vol. 2(1), pp. 83-94.
Henneman et al., Phase analysis of gated myocardial perfusion single-photon emission computed tomography compared with tissue doppler imaging for the assessment of left ventricular dyssynchrony, Journal of the American College of Cardiology, Apr. 2007, vol. 49 (16), pp. 1708-1714.
Kingdom et al., Sensitivity to contrast histogram differences in synthetic wavelet-textures, Vision Research, Mar. 2001, vol. 41(5), pp. 585-598.
Li et al., Cross-frequency coupling during isoflurane anaesthesia as revealed by electroencephalographic harmonic wavelet bicoherence, Neurosciences and Neuroanaesthesia, British Journal of Anaesthesia, Mar. 2013, vol. 110(3), pp. 409-419.
Moore, A modification of the Rayleigh test for vector data, Biometrika, Apr. 1980, vol. 67(1), pp. 175-180.
Mousavi et al., A wavelet transform based method to determine depth of anesthesia to prevent awareness during general anesthesia, Computational and Mathematical Methods in Medicine, 2014, vol. 2014, pp. 1-13.
Rakhmanov et al., A cross-correlation method for burst searches with networks of misaligned gravitational-wave detectors, Institute of Physics Publishing, Classical and Quantum Gravity, Sep. 6, 2005, vol. 22(18), pp. S1311-S1320.
Wang et al., The residual phase estimation of a seismic wavelet using a renyi divergence-based criterion, Journal of Applied Geophysics, Jul. 2014, vol. 106, pp. 96-105.
Yu, Histogram Matching Seismic Wavelet Phase Estimation, May 2012, Masters thesis, University of Houston.
Anor et al., Modeling of blood flow in arterial trees, Focus Article, WIREs Systems Biology and Medicine, Sep./Oct. 2010, vol. 2, pp. 612-623.
Hamberg et al., Quantitative high-resolution measurement of cerebrovascular physiology with slip-ring CT, AJNR Am J Neuroradiol, Apr. 1996, vol. 17(4), pp. 639-650.
Kashif et al., Model-based non-invasive estimation of intracranial pressure from cerebral blood flow velocity and arterial pressure, Science Translational Medicine, Apr. 2012, vol. 4(129): 129ra44.
Lassen et al., Tracer Kinetic Methods in Medical Physiology, 1979, Raven Press, New York.
Linninger et al., A mathematical model of blood, cerebrospinal fluid and brain dynamics, J Mathematical Biology, Dec. 2009, vol. 59(6), pp. 729-759.
Bayer et al., Two-dimensional simulations of displacement accumulation incorporating shear strain, Ultrason imaging, Jan. 2014, vol. 36(1), pp. 55-73.
Braun et al., High-resolution mechanical imaging of the human brain by three-dimensional multifrequency magnetic resonance elastography at 7T, NeuroImage, Apr. 2014, vol. 90, pp. 308-314.
Feingold et al., Quantitative volumetric perfusion mapping of the microvasculature using contrast ultrasound, Invest Radiol, Oct. 2010, vol. 45(10), pp. 669-674.
Gauthier et al., Assessment of quantitative perfusion parameters by dynamic contrast-enhanced sonography using a deconvolution method, an in vitro and in vivo study, J Ultrasound Med, Apr. 2012, vol. 31(4), pp. 595-608.
Johnson et al., Local mechanical properties of white matter structures in the human brain, NeuroImage, Oct. 2013, vol. 79, pp. 145-152.
Ashmead, Morelet Wavelets in quantum mechanics, Quanta, Nov. 2012, vol. 1, Issue 1, pp. 58-70.
Johnstone et al., Wavelet threshold estimators for data with correlated noise, Journal of the Royal Statistical Society: Series B (Statistical Methodology), 1997, 59(2), pp. 319-351.
Khullar et al., Wavelet-based fMRI analysis: 3-d denoising, signal separation, and validation metrics, NeuroImage, Feb. 2011, vol. 54(4), pp. 2867-2884.
Abdallah, Considerations in perioperative assessment of valproic acid coagulopathy, review article, Journal of Anaesthesiology Clinical Pharmacology, Jan.-Mar. 2014, vol. 30, iss. 1, pp. 7-9.
D'Agnolo et al., Radon-Penrose transform for D-modules, Sep. 6, 1994, pp. 1-37.
Penkov, A Geometric Approach to the Linear Penrose Transform, Transactions of the American Mathematical Society, Aug. 1985, vol. 290, No. 2, pp. 555-575.
Wolfram, Statistical mechanics of cellular automata, The American Physical Society, Reviews of Modern Physics, vol. 55, No. 3, Jul. 1983, pp. 601-644.
Sturm et al., New Brain Tumor Entities Emerge from Molecular Classification of CNS-PNETs, Cell, Feb. 25, 2016, vol. 164, iss. 5, pp. 1060-1072.
Liebling et al., Wavelet-based Synchronization of Nongated Confocal Microscopy Data for 4D Imaging of the Embryonic Heart, Proceedings of SPIE 5914, Wavelets XI, 2005, vol. 591409, 6 pages.

(56) References Cited

OTHER PUBLICATIONS

Ehrenreich et al., New developments in the understanding of cerebral vasoregulation and vasospasm: the endothelin-nitric oxide network, CME Credit, Cleveland Clinic Journal of Medicine, Mar.-Apr. 1995, vol. 62, No. 2, pp. 105-116.

Vagharshakyan et al., Light Field Reconstruction Using Shearlet Transform, Sep. 29, 2015, pp. 1-12 (Cornell University Archive, https://arxiv.org/abs/1509.08969, arXiv:1509.08969v1).

Daubechies, Orthonormal Bases of Compactly Supported Wavelets, Communications on Pure and Applied Mathematics, 1988, vol. XLI, pp. 909-996.

Mandelshtam, The Multidimensional Filter Diagonalization Method, Journal of Magnetic Resonance, 2000, vol. 144, pp. 343-356.

Insolera et al., Cortical neurogenesis in the absence of centrioles, Nat Neurosci, Nov. 2014, vol. 17, No. 11, pp. 1528-1536.

Kool et al., Molecular subgroups of medulloblastoma: an international meta-analysis of transcriptome, genetic aberrations, and clinical data of WNT, SHH, Group 3, and Group 4 medulloblastomas, 2012, Acta Neuropathol, vol. 123, pp. 473-484.

Kutyniok et al., Compactly Supported Shearlets, Approximation Theory XIII: San Antonio 2010, pp. 1-24.

Liner, An overview of wavelet transform concepts and applications, University of Houston, Feb. 26, 2010, pp. 1-17.

Liu et al., Motion Magnification, ACM Transactions on Graphics (TOG), Jul. 2005, vol. 24, iss. 3, pp. 519-526 (8 pages).

Lohani et al., Intrasacral meningocele in the pediatric population, J Neurosurg Pediatrics, Jun. 2013, vol. 11, pp. 615-622.

Long et al., Spatiotemporal wavelet analysis for functional MRI, NeuroImage, 2004, vol. 23, pp. 500-516.

Maltz et al., Fixed gantry tomosynthesis system for radiation therapy image guidance based on a multiple source x-ray tube with carbon nanotube cathodes, Medical Physics, May 2009, vol. 36, No. 5, pp. 1624-1636.

Mandelshtam, FDM: the filter diagonalization method for data processing in NMR experiments, Progress in Nuclear Magnetic Resonance Spectroscopy, 2001, vol. 38, pp. 159-196.

Mourant et al., Hemoglobin parameters from diffuse reflectance data, Journal of Biomedical Optics, Mar. 2014, vol. 19, No. 3, pp. 037004-1-037004-9.

D'Ariano, How to Derive the Hilbert-Space Formulation of Quantum Mechanics From Purely Operational Axioms, 20 pages (presented at conference "On the Present Status of Quantum Mechanics" held on Sep. 7-9, 2005, Mali Losinj, Croatia) (Cornell University Archive, https://arxiv.org/abs/quant-ph/0603011, arXiv:quant-ph/0603011v1).

Mixter, Ventriculoscopy and Puncture of the Floor of the Third Ventricle, Boston M. & S. Journal, Mar. 1, 1923, vol. 188, No. 9, pp. 277-278.

Moussa et al., Efficacy of postoperative antibiotic injection in and around ventriculoperitoneal shunt in reduction of shunt infection: A randomized controlled trial, Clinical Neurology and Neurosurgery, 2016, vol. 143, pp. 144-149.

Monici, Cell and tissue autofluorescence research and diagnostic applications, Biotechnology Annual Review, 2005, vol. 11, pp. 227-256.

Drexler et al., In vivo ultrahigh-resolution optical coherence tomography, Optics Letters, Sep. 1, 1999, vol. 24, No. 17, pp. 1221-1223.

Rees et al., Role of endothelium-derived nitric oxide in the regulation of blood pressure, Proc. Natl. Acad. Sci. USA, 1989, vol. 86, pp. 3375-3378.

Rodino et al., The Gabor Wave Front Set (2013) (Cornell University Archive, https://arxiv.org/abs/1207.5628, arXiv:1207 5628v2), pp. 1-29.

Schaer et al., Haptoglobin Preserves Vascular Nitric Oxide Signaling during Hemolysis, American Journal of Respiratory and Critical Care Medicine, May 15, 2016, vol. 193, iss 10, pp. 1111-1122.

Shumacher, Analog clock and watch reader, 2015, pp. 1-10 (https://www.cs.bgu.ac.il/~ben-shahar/Teaching/Computational-Vision/StudentProjects/ICBV151/ICBV-2015-1-ChemiShumacher/Report.pdf).

Tudor et al., Endoscopic third ventriculostomy (ETV) for idiopathic normal pressure hydrocephalus (iNPH) (Review), Cochran Collection, Cochrane Database of Systematic Reviews, 2015, iss. 7, pp. 1-23.

Khandelwal et al., Age-dependent increase in green autofluorescence of blood erythrocytes, J. Biosci. Sep. 2007, vol. 32, No. 6, pp. 1139-1145.

Wadhwa et al., Phase-Based Video Motion Processing, MIT Computer Science and Artificial Intelligence Lab, ACM Transactions on Graphics, Jul. 2013, vol. 32, No. 4, article 80, pp. 80:1-80:9.

Yang et al., Improved phase-resolved optical Doppler tomography using the Kasai velocity estimator and histogram segmentation, Optics Communications, Jul. 15, 2002, vol. 208, pp. 209-214.

Zhang et al., Orthogonal Complex Filter Banks and Wavelets: Some Properties and Design, IEEE Transactions on Signal Processing, Apr. 1999, vol. 47, No. 4, pp. 1039-1048.

Aaslid et al., Cerebral Autoregulation Dynamics in Humans, Stroke, 1989, vol. 20, pp. 45-52.

Adams et al., Symptomatic Occult Hydrocephalus with "Normal" Cerebrospinal-Fluid Pressure, A Treatable Syndrome, The New England Journal of Medicine, Jul. 15, 1965, vol. 273, No. 3, pp. 117-126.

Barina, Gabor Wavelets in Image Processing, Feb. 10, 2016, 6 pages (Cornell University Archive, https://arxiv.org/pdf/1602.03308.pdf, arXiv:1602.03308v1).

Bernardes et al., Digital Ocular Fundus Imaging: A Review, Ophthalmologica, 2011, vol. 226, pp. 161-181.

Bernardino et al., A Real-Time Gabor Primal Sketch for Visual Attention, Second Iberian Conference on Pattern Recognition and Image Analysis, 2005, 8 pages (http://vislab.isr.ist.utl.pt/publications/05-ibpria-alex.pdf).

Guo et al., Wavelets with composite dilations and their MRA properties, Applied and Computational Harmonic Analysis, 2006, vol. 20, pp. 202-236.

Goh et al., Subependymal giant cell tumors in tuberous sclerosis complex, Neurology, Oct. 2004, vol. 63, pp. 1457-1461.

Bo et al., Symbolic Representations in Motor Sequence Learning, Neuroimage, 2011, vol. 54, No. 1, pp. 417-426.

Bodranghien et al., Consensus Paper: Revisiting the Symptoms and Signs of Cerebellar Syndrome, Cerebellum, Jun. 2016, vol. 15, No. 3, pp. 369-391 (published online Jun. 2015) (23 pages).

Borsdorf et al., Separate CT-Reconstructions for 3D Wavelet Based Noise Reduction Using Correlation Analysis, 2007, IEEE Nuclear Science Symposium Conference Record, pp. 2633-2638.

Brouder et al., A Smooth Introduction to the Wavefront Set, Apr. 7, 2014, pp. 1-29 (Cornell University Archive, https://arxiv.org/pdf/1404.1778.pdf, arXiv:1404.1778v1).

Burt et al., The Laplacian Pyramid as a Compact Image Code, IEEE Transactions on Communications, Apr. 1983, vol. COM-31, No. 4, pp. 532-540.

Candes et al., New Tight Frames of Curvelets and Optimal Representations of Objects with C2 Singularities, Nov. 2002, pp. 1-39 (http://citeseerx.ist.psu.edu/viewdoc/download?doi=10.1.1.162.1548&rep=rep1&type=pdf).

Cense et al., Ultrahigh-resolution high-speed retinal imaging using spectral-domain optical coherence tomography, Optics Express, May 31, 2004, vol. 12, No. 11, pp. 2435-2447 (13 pages).

Cheng et al., Mammalian DNA Methyltransferases: A Structural Perspective, Structure, Review, Mar. 2008, vol. 16, No. 3, pp. 341-350.

Coumans et al., Volumetric analysis of syringomyelia following hindbrain decompression for Chiari malformation Type I: syringomyelia resolution follows exponential kinetics, Neurosurg Focus, Sep. 2011, vol. 31, No. 3:E4, pp. 1-4.

Dahmen, Wavelet and Multiscale Methods for Operator Equations, 1997 (146 pages).

Deutsch et al., Information Flow in Entangled Quantum Systems, (1999) pp. 1-24 (https://arxiv.org/ftp/quant-ph/papers/9906/9906007-pdf).

Donoho, Compressed Sensing, Sep. 14, 2004, pp. 1-34.

Donoho et al., Message-Passing Algorithms for Compressed Sensing, PNAS, Nov. 10, 2009, vol. 106, No. 45, pp. 18914-18919.

(56) References Cited

OTHER PUBLICATIONS

Duverger et al., Concentrations of Putative Neurovascular Transmitters in Major Cerebral Arteries and Small Pial Vessels of Various Species, Journal of Cerebral Blood Flow and Metabolism, 1987, vol. 7, No. 4, pp. 497-501.
Eastwood, The Penrose Transform for Complex Projective Space, Cornell University Archive, Aug. 17, 2008, pp. 1-11 (https://arxiv.org/abs/0808.2321, arXiv:0808.2321v1).
Eastwood et al., Cohomology and Massless Fields, Commun. Math. Phys. (1981) vol. 78, pp. 305-351.
Edelman et al., Nitric Oxide: Linking Space and Time in the Brain, Proc. Natl. Acad. Sci. USA, Dec. 1992, vol. 39, pp. 11651-11652.
Feichtinger et al., Gabor Frames and Time-Frequency Analysis of Distributions, Journal of Functional Analysis, 1997, vol. 146, No. FU963078, pp. 464-495.
Feng et al., Conservation and Divergence of Methylation Patterning in Plants and Animals, PNAS, May 11, 2010, vol. 107, No. 19, pp. 8689-8694.
Fisher et al., Group Formation, Relatedness, and the Evolution of Multicellularity, Current Biology, Jun. 17, 2013, vol. 23, No. 12, pp. 1120-1125.
Fujimoto et al., Optical Coherence Tomography: An Emerging Technology for Biomedical Imaging and Optical Biopsy, Neoplasia, Jan.-Apr. 2000, vol. 2, Nos. 1-2, pp. 9-25.
Goriely et al., Mechanics of the brain: perspectives, challenges, and opportunities, Biomech Model Mechanobiol, 2015, vol. 14, pp. 931-965.
Guerquin-Kern et al., A Fast Wavelet-Based Reconstruction Method for Magnetic Resonance Imaging, IEEE Transactions on Medical Imaging, Institute of Electrical and Electronics Engineers, 2011, 14 pages (obtained from HAL archives-ouvertes).
Guo et al., Sparse Multidimensional Representations using Anisotropic Dilation and Shear Operators, 2005, 13 pages (https://www.math.uh.edu/~dlabate/Athens.pdf).
Han, Properties of Discrete Framelet Transforms, Math. Model. Nat. Phenom., 2013, vol. 8, No. 1, pp. 18-47 (32 pages).
Heil, What is a Frame?, Notices of the AMS, 2013, vol. 60, No. 6, pp. 748-750.
Herz et al., Ultrahigh resolution optical biopsy with endoscopic optical coherence tomography, Optics Express, Jul. 26, 2004, vol. 12, No. 15, pp. 3532-3542.
Hogeweg, Cellular Automata as a Paradigm for Ecological Modeling, Applied Mathematics and Computation, 1988, vol. 27, pp. 81-100.
Hormander, The Spectral Function of an Elliptic Operator, Acta Math, May 7, 1968, vol. 121, pp. 193-218.
Huff et al., Dnmt1-Independent CG Methylation Contributes to Nucleosome Positioning in Diverse Eukaryotes, Cell, Mar. 13, 2014, vol. 156, No. 6, pp. 1286-1297.
Januszewski et al., Flow-based evalution of cerebral revascularization using near-infrared indocyanine green videoangiography, Neurosurg Focus, Feb. 2014, vol. 36, No. 2: E14, pp. 1-8.
Jia et al., Quantitative OCT angiography of optic nerve head blood flow, Biomedical Optics Express, Dec. 1, 2012, vol. 3, No. 12, pp. 3127-3137.
Kamble et al., A Review: Eulerian Video Motion Magnification, International Journal of Innovative Research in Computer and Communication Engineering, Mar. 2015, vol. 3, iss. 3, pp. 2384-2390.
Kim et al., Epigenetic mechanisms in mammals, Cellular and Molecular Life Sciences, 2009, vol. 66, pp. 596-612.
Kittipoom et al., Construction of Compactly Supported Sheariet Frames, Cornell University Archive, 2010, pp. 1-37 (https://arxiv.org/abs/1003.5481, arXiv:1003.5481v2).
Klimenko et al., A cross-correlation technique in wavelet domain for detection of stochastic gravitational waves, 2002, pp. 1-15 (https://arxiv.org/abs/gr-qc/0208007, arXiv:gr-qc/0208007v1).
Knopfmacher et al., Graphs, partitions and Fibonacci numbers, Discrete Applied Mathematics, 2007, vol. 155, pp. 1175-1187.
Koenig et al., Regression of Subependymal Giant Cell Astrocytoma With Rapamycin in Tuberous Sclerosis Complex, J Child Neurol., Oct. 2008, vol. 23, No. 10, pp. 1238-1239.
Kramer et al., Intraventricular fibrinolysis with tissue plasminogen activator is associated with transient cerebrospinal fluid inflammation: a randomized controlled trial, Journal of Cerebral Blood Flow & Metabolism, 2015, vol. 35, pp. 1241-1248.
Kutyniok et al., Resolution of the Wavefront Set using Continuous Sheariets, Transactions of the American Mathematical Society, May 2009, vol. 361, No. 5, pp. 2719-2754.
Kutyniok et al., Image Separation using Wavelets and Sheariets, International Conference on Curves and Surfaces, 2010, pp. 1-14 (https://www.math.tu-berlin.de/fileadmin/i26_fg-kutyniok/Kutyniok/Papers/ImageSeparation.pdf).
Lee, Wavelet-Vaguelette Decompositions and Homogeneous Equations, Dec. 1997, Purdue University, In Partial Fulfillment of the Requirements for the Degree of Doctor of Philosophy, 103 pages.
Lindenmayer, Developmental Algorithms for Multicellular Organisms: A Survey of L-Systems, J. Theor. Biol., 1975, vol. 54, pp. 3-22.
Lopez et al., The Cauchy problem for a forced harmonic oscillator, Revista Mexicana De Fisica, Dec. 2009, vol. 55, No. 2, pp. 196-215.
Luney et al., Acute Posterior Cranial Fossa Hemorrhage—Is Surgical Decompression Better than Expectant Medical Management?, Neurocritical Care, Apr. 12, 2016, 6 pages.
Gabor, Theory of Communication, Part 3: Frequency Compression and Expansion, 1946, vol. 93, No. 26, pp. 445-457.
Havla et al., Wavelet-based calculation of cerebral angiographic data from time-resolved CT perfusion acquisitions, Eur Radiol. Aug. 2015, vol. 25, No. 8, pp. 2354-2361 (published online Feb. 26, 2015) (8 pages).
Kamp et al., Microscope-Integrated Quantitative Analysis of Intraoperative Indocyanine Green Fluorescence Angiography for Blood Flow Assessment: First Experience in 30 Patients, Operative Neurosurgery 1, vol. 70, Mar. 2012, pp. ons65-ons74.
Mazzola et al., Pediatric Hydrocephalus: systematic literature review and evidence-based guidelines. Part 2 Management of posthemorrhagic hydrocephalus in premature infants, Nov. 2014, J Neurosurg Pediatrics (Suppl), vol. 14, pp. 8-23.
McCrory et al., Consensus statement on concussion in sport: the 4th International Conference on Concussion in Sport held in Zürich, Nov. 2012, Br J Sports Med, (2013), vol. 47, pp. 250-258.
Michod et al., Cooperation and Conflict in the Evolution of Multicellularity, 2001, The Genetics Society of Great Britain, Heredity, vol. 86, pp. 1-7.
Nehra et al., Peyronie's Disease: AUA Guideline, American Urological Association (AUA) Guideline, approved Apr. 2015, pp. 1-41.
Butler, W.E., "Wavelet brain angiography suggests arteriovenous pulse wave phase locking," PLOS ONE, vol. 12, No. 11, Nov. 15, 2017 (16 pages).
Hyvärinen, L., et al., "Indocyanine green fluorescence angiography." Acta ophthalmologica, vol. 58, No. 4, pp. 528-538, 1980 (11 pages).
Desmettre, T., et al., "Fluorescence properties and metabolic features of indocyanine green (ICG) as related to angiography," Survey of ophthalmology, vol. 45, No. 1, pp. 15-27, Jul. 2000 (13 pages).
Kuroiwa, T et al., "Development and clinical application of near-infrared surgical microscope: preliminary report," Minimally Invasive Neurosurgery, vol. 44, No. 4, pp. 240-242, 2001. Abstract accessed online on Jun. 16, 2020 at <http://www.thieme-connect.de/DOI/DOI?10.1055/s-2001-19929> (2 pages).
Mourant, J. et al., "Hemoglobin parameters from diffuse reflectance data," Journal of Biomedical Optics, vol. 19, No. 3, p. 037004, 2014 (10 pages).
Robles, E., et al., "Assessing hemoglobin concentration using spectroscopic optical coherence tomography for feasibility of tissue diagnostics," Biomedical Optics Express, vol. 1, No. 1, p. 310, 2010 (8 pages).
Lahiri, B., et al., "Medical applications of infrared thermography: A review," Infrared Physics & Technology, vol. 55, No. 4, pp. 221-235, Jul. 2012 (16 pages).
Bachmann, L. et al., "Fluorescence Spectroscopy of Biological Tissues: A Review," Applied Spectroscopy Reviews, vol. 41, No. 6, pp. 575-590, Jul. 2006 (16 pages).

(56) References Cited

OTHER PUBLICATIONS

Devor, A., et al., "Frontiers in optical imaging of cerebral blood flow and metabolism," Journal of Cerebral Blood Flow and Metabolism, vol. 32, No. 7, pp. 1259-1276, Jan. 18, 2012 (18 pages).
Chen, Z., et al., "Optical Doppler tomography," IEEE Journal on Selected Topics in Quantum Electronics, vol. 5, No. 4, pp. 1134-1142, Jul. 1, 1999 (10 pages).
Yazdanfar, S., et al., "High resolution imaging of in vivo cardiac dynamics using color Doppler optical coherence tomography," Optics Express, vol. 1, No. 13, pp. 424-431, Dec. 22, 1997 (8 pages).
Chen, C., et al., "Optical coherence tomography based angiography [Invited]," Biomedical Optics Express, vol. 8, No. 2, p. 1056, Jan. 24, 2017 (27 pages).
Makita, S., et al., "Optical coherence angiography," Optics Express, vol. 14, No. 17, pp. 114-116, Aug. 21, 2006 (20 pages).
Zhao, Y., et al., "Phase-resolved optical coherence tomography and optical Doppler tomography for imaging blood flow in human skin with fast scanning speed and high velocity sensitivity," Optics Letters, vol. 25, No. 2, pp. 114-116, Jan. 15, 2000 (4 pages).
Chen, Z., et al., "Noninvasive imaging of in vivo blood flow velocity using optical Doppler tomography," Optics Letters, vol. 22, No. 14, Jul. 15, 1997 (3 pages).
Izatt, J., et al., "In vivo bidirectional color Doppler flow imaging of picoliter blood volumes using optical coherence tomography," Optics Letters, vol. 22, No. 18, Sep. 15, 1997 (3 pages).
Drexler, W., "Ultrahigh-resolution optical coherence tomography," Journal of Biomedical Optics 9(1), 47-74, Jan./Feb. 2004 (28 pages).
Wang, R., et al., "Phase-sensitive optical coherence elastography for mapping tissue microstrains in real time," Applied Physics Letters, vol. 90, No. 16, Apr. 19, 2007 (4 pages).
Wu, H., et al., "Eulerian Video Magnification for Revealing Subtle Changes in the World," Association for Computing Machinery, vol. 31, No. 4, pp. 1-8, Jul. 2012 (9 pages).
Nielsen, Conditions for A Class of Entanglement Transformations, Aug. 17, 1999, pp. 1-4 (Cornell University Archive, arXiv No. quant-ph/9811053v2).
Novotny et al., A Method of Photographing Fluorescence in Circulating Blood in the Human Retina, Circulation, vol. XXIV, Jul. 1961, pp. 82-86.
Pewsey et al., Circular Statistics in R, Oxford University Press, (2013) Chapters 1-3, 7 and Appendix (80 pages).
Pfister et al., Molecular diagnostics of CNS embryonal tumors, Acta Neuropathology, Nov. 2010, vol. 120, No. 5, pp. 553-566.
Pollock, Dyadic Wavelets Analysis, (2016) pp. 1-26.
Qian et al., High Resolution Stationary Digital Breast Tomosynthesis using Distributed Carbon Nanotube X-ray Source Array, Medical Physics, (Apr. 2012) vol. 39, No. 4, pp. 2090-2099.
Rashid-Farrokhi et al., Wavelet-Based Multiresolution Local Tomography, IEEE Transactions on Image Processing, Oct. 1997, vol. 6, No. 10, pp. 1412-1430.
Rollins et al., Real-time in vivo color Doppler optical coherence tomography, Journal of Biomedical Optics, Jan. 2002, vol. 7, No. 1, pp. 123-129.
Ronneberger et al., U-Net: Convolutional Networks for Biomedical Image Segmentation, May 18, 2015, pp. 1-8 (Cornell University Archive, arXiv No. 1505.04597v1).
Ruzhansky, Introduction to pseudo-differential operators, Jan. 21, 2014, pp. 1-54.
Sadowsky, The Continuous Wavelet Transform: A Tool for Signal Investigation and Understanding, John Hopkins APL Technical Digest, 1994, vol. 15, No. 4, pp. 306-318.
Saito et al., Efficient Gene Transfer into the Embryonic Mouse Brain Using in Vivo Electroporation, Developmental Biology, 2001, vol. 240, pp. 237-246.
Sen et al., 3D ROI Image Reconstruction from Truncated Computed Tomogrpahy, IEEE Transactions on Medical Imaging, May 26, 2013, pp. 1-24.
Shen et al., Growth hormone therapy and risk of recurrence/progression in intracranial tumors: a meta-analysis, Neurol Sci, 2015, vol. 36, pp. 1859-1867.
Shy et al., X-Y separable pyramid steerable scalable kernels, (1994) pp. 237-244 (https://authors.library.caltech.edu/3438/1/SHYcvpr94.pdf).
Valens, A Really Friendly Guide to Wavelets, 1999, pp. 1-19.
Vrhel et al., Fast Computation of the Continuous Wavelet Transform through Oblique Projections, (1996) pp. 1-4 (http://citeseerx.ist.psu.edu/viewdoc/download?doi=10.1.1.66.3780&rep=rep1&type=pdf).
Wang et al., Three dimensional optical angiography, Optics Express, Apr. 2, 2007, vol. 15, No. 7, pp. 4083-4097.
Wang et al., Doppler optical micro-angiography for volumetric imaging of vascular perfusion in vivo, May 25, 2009, Optics Express, vol. 17, No. 11, pp. 8926-8940.
Wunsch, Microlocal Analysis and Evolution Equations: Lecture Notes from 2008 CMI/ETH Summer School, 2012 (92 pages).
Yang et al., The X-Ray Transform Projection of 3D Mother Wavelet Function, Research Article, Computational and Mathematical Methods in Medicine, 2013, Article ID 754829, 9 pages.
Zhu et al., Endothelial nitric oxide synthase: a potential therapeutic target for cerebrovascular diseases, Molecular Brain, 2016, vol. 9, No. 30, pp. 1-8.
Zhuang et al., Fan-beam and cone-beam image reconstruction via filtering the backprojection image of differentiated projection data, Institute of Physics Publishing, Physics in Medicine and Biology, 2004, vol. 49, pp. 5489-5503.
Taylor et al., Molecular subgroups of medulloblastoma: the current consensus, Consensus Paper, Acta Neuropathol, 2012, vol. 123, pp. 465-472.
Thavavel et al., Regularized Computed Tomography using Complex Wavelets, International Journal of Magnetic Resonance Imaging, 2007, vol. 1, No. 1, pp. 027-032.
Thielen et al., Ultrafast dynamic computed tomography myelography for the precise identification of high-flow cerebrospinal fluid leaks caused by spiculated spinal osteophytes, J Neurosurg Spine, Clinical Article, Mar. 2015, vol. 22, pp. 324-331.
Spaide et al., Retinal Vascular Layers Imaged by Fluorescein Angiography and Optical Coherence Tomography Angiography, Original investigation, JAMA Opthalmology, Jan. 2015, vol. 133, No. 1, pp. 45-50.
Ren et al., Phase-resolved functional optical coherence tomography: simultaneous imaging of in situ tissue structure, blood flow velocity, standard deviation, birefirngence, and Stokes vectors in human skin, Optics Letters, Oct. 1, 2002, vol. 27, No. 19, pp. 1702-1704.
Shenoi, Introduction to Digital Signal Processing and Filter Design, Wiley, 2006, Chapters 3-5 (217 pages).
Srinivasan et al., Quantitative Cerebral Blood Flow with Optical Coherence Tomography, Optics Express, Feb. 1, 2010, vol. 18, No. 3, pp. 2477-2494.
Steane, An introduction to spinors, Dec. 13, 2013, pp. 1-23 (Cornell University Archive, arXiv No. 1312.3824v1).
Thompson et al., Prognostic Value of Medulloblastoma Extent of Resection After Accounting for Molecular Subgroup: A Retrospective Integrated Clinical and Molecular Analysis, Lancet Oncol. Apr. 2016, vol. 17, No. 4, pp. 484-495.
Timmons, Image-Guided Neurosurgery: Integration of Medical Image Data with a Real-time View of the Surgical Field, Jun. 1997, pp. 1-66.
Tran et al., Learning Spatiotemporal Features with 3D Convolutional Networks, Proceedings of the 2015 IEEE International Conference on Computer Vision (ICCV), (2015) pp. 4489-4497.
Rao et al., Shear strain imaging using shear deformations (2008) Med. Phys. 35(2):412-423.
Weaver et al., Brain mechanical property measurement using MRE with intrinsic activation Phys. Med. Biol. (2012) 57:7275-7287.
Kashif et al., Model-Based Noninvasive Estimation of Intracranial Pressure from Cerebral Blood Flow Velocity and Arterial Pressure, Sci. Transl. Med. (2012) vol. 4, No. 129, pp. 1-10.
Bayer et al., Two-Dimensional Simulations of Displacement Accumulation Incorporating Shear Stain, Ultrason. Imaging (2014) vol. 36(1):55-73.

(56) References Cited

OTHER PUBLICATIONS

Feingold et al., Quantitative volumetric perfusion mapping of the microvasculature using contrast ultrasound, Invest Radiol. (2010)45:669-674.
Johnson et al., Local mechanical properties of white matter structures in the human brain, NeuroImage (2013) 79:145-152.
Khullar et al., Wavelet-based fMRI analysis: 3-D denoising, signal seperation, and validation metrics, NeuroImage (2011)54:2867-2884.
Lee et al., Wavelet Methods for Inverting the Radon Transform with Noisy Data, IEEE Transactions on Image Processing, (2001) vol. 10, No. 1, pp. 79-94 (16 pages) (https://www.math.purdue.edu/~lucier/692/tomography.pdf).
Kutyniok et al., ShearLab 3D: Faithful Digital Shearlet Transforms based on Compactly Supported Shearlets, (2014) (39 pages) (Cornell University Archive, arXiv No. 1402.5670v1).
R-Forge User's Manual, (2011), SVN Revision: 227, 10 pages.
Daubechies Ten Lectures of Wavelets, Springer-Verlag, (1992), from CBMS-NSF Regional Conference Series in Applied Mathematics Society for Industrial and Applied Mathematics 1990 (344 pages).
Lawton, Seven Aneurysms Tenets and Techniques for Clipping (2011) Section 1, Thieme Medical Publishers, New York, Section 1, (36 pages).
Forbes et al., Statistical Distributions, Fourth Edition, copyright 2011, John Wiley and Sons, Inc., Chapters 1-9, (84 pages).
Mandelshtam et al., Harmonic inversion of time signals and its applications, AIP The Journal of Chemical Physics 1997, vol. 107, No. 6756, 12 pages.
Schroeder, The Simple Harmonic Oscillator, copyright 2015-2016, 5 pages (https://physics.weber.edu/schroeder/quantum/Harmonic pdf).
International Standards Organization, ISO/IEC 14496-12 Multimedia Formats Information Technology—Coding of audio-visual objects (2008) 4 pages (Abstract).
Guido et al., Introduction to the special issue on wavelet-based algorithms for medical problems (2007) vol. 37, p. 429.
Zhang et al., "Application of Wavelet Thresholding De-noising in DSA," International Symposium on Information Science and Engineering IEEE Computer Society, 2008, pp. 130-134.
Akram et al., "Blood Vessel Enhancement and Segmentation Using Wavelet Transform, International Conference on Digital Image Processing IEEE Computer Society," 2009, pp. 34-38.
Cao et al., "Joint Spatio-Temporal Registration and Microvasculature Segmentation of Retinal Angiogram Sequences," 33rd Annual International Conference of the IEEE EMBS, 2011, pp. 2618-2621.
Tsai et al., "Motion Estimation and Wavelet Transform in Angiogram Video Coding," IEEE, 1994, pp. 1121-1125.
Oh et al., "Reversible Wavelet Compression For Digital Angiograms," Proceedings of the 20th Annual International Conference of the IEEE Engineering in Medicine and Biology Society,1998, vol. 20, No. 3, pp. 1442-1445.
Tache et al., "Enhanced Visualization of Cerebral Blood Vessels for X-ray Angiograms," IEEE International Conference on E-Health and Bioengineering, 2013, pp. 1-13.
Sun et al., "Morphological enhancement of vascular angiogram with multiscale detected by Gabor filters," Electronics Letters, 2008, vol. 44, No. 2, pp. 1-3.
Munteanu et al., "Wavelet-Based Lossless Compression of Coronary Angiographic Images," IEEE Transactions on Medical Imaging, 1999, vol. 18, No. 3, pp. 272-281.
Lin et al., "Extraction of Coronary Arterial Tree Using Cine X-Ray Angiograms," Biomedical Engineering-Applications, Basis & Communications, 2005, pp. 111-120.
Hohne et al., "Fourier Domain Techniques for Digital Angiography of the Heart," IEEE Transactions on Medical Imaging, 1984, vol. MI-3, No. 2, pp. 62-67.
Hohne et al., "Proceedings of SPIE: Digital Angiography of The Heart In The Frequency Domain," Medical Images and Icons IEEE, 1984, pp. 245-250.
Havla et al., "Validation of a method to differentiate arterial and venous vessels in CT perfusion data using linear combinations of quantitative time-density curve characteristics," Eur. Radiol, 2015, vol. 25, pp. 2937-2944.
Farge, M., "Wavelet Transforms and Their Applications to Turbulence," Annu. Rev. Fluid Mech., 1992, vol. 24, pp. 395-457.
Havla, et al., "Classification of arterial and venous cerebral vasculature based on wavelet postprocessing of CT perfusion data," Med. Phys. (2016) 43 (2), pp. 702-709.

\* cited by examiner

RECONSTRUCTING CARDIAC FREQUENCY PHENOMENA IN ANGIOGRAPHIC DATA

CROSS-REFERENCE TO RELATED APPLICATIONS

This application claims priority to U.S. Provisional Application No. 62/824,582, filed Mar. 27, 2019, the contents of which are hereby incorporated by reference in their entirety.

FIELD

The field generally relates to techniques for reconstructing cardiac frequency phenomena within an angiographic study, and in particular, to techniques that utilize bandpass filters and/or amplification to isolate and/or magnify the cardiac frequency phenomena within an angiographic study.

BACKGROUND OF THE INVENTION

To obtain an angiogram, a bolus of a chemical contrast agent is injected intravascularly into a patient, and a sequence or time series of x-rays is obtained. Two-dimensional projections of the anatomy of the vascular system are captured as the chemical contrast agent, which blocks the passage of x-rays, passes through the vascular system in the x-ray projection path. The aggregation of these images sequenced according to time of acquisition comprises an angiogram.

As described in U.S. Pat. No. 10,123,761 (hereinafter "the '761 patent"), which is incorporated by reference herein in its entirety, fluoroscopic angiographic imaging captures and quantifies cardiac frequency phenomena allowing spatiotemporal reconstruction of a moving vascular pulse wave in the brain and other organs using wavelets for processing the angiographic data. This technique allows for visualization of blood flow as a sequence of arterial stroke volumes, through the capillary bed and as a sequence of venous pulse volumes of reciprocal cardiac phase. Thus, the spatial and temporal distribution of cardiac frequency phenomena in blood flow provides physiological, diagnostic and medical information that may be shown in cine images of an angiogram.

While the above described technique provides a spatiotemporal reconstruction of a moving vascular pulse wave in the brain and other organs, it is desirable to develop other methods for reconstructing the cardiac frequency phenomena within an angiographic study so as to provide for greater flexibility to existing techniques.

BRIEF DESCRIPTION OF THE INVENTION

Embodiments of the invention are directed to methods, systems, and computer readable media for reconstructing cardiac frequency phenomena in angiographic data that do not utilize wavelets, and in particular Gabor wavelets, for processing angiographic data.

A system, method, and computer readable for extracting cardiac frequency angiographic phenomena from an angiographic study obtained at a rate faster than cardiac frequency is provided. Angiographic data is obtained or received from an angiographic study obtained at a rate faster than cardiac frequency and a cardiac frequency bandpass filter is applied to the angiographic data to output a spatiotemporal reconstruction of cardiac frequency angiographic phenomena, which may then be displayed in one or more images.

In accordance with another aspect, a Eulerian magnification may be applied to the angiographic data in order to yield an amplified effect. The Eulerian magnification may be applied to angiographic images in order to select for those with temporal and spatial phenomena of interest, including temporal phenomena corresponding to the cardiac frequency band.

In accordance with another aspect, applying the cardiac frequency bandpass filter extracts the cardiac frequency angiographic phenomena from a cine sequence of angiographic images.

In accordance with another aspect, applying the cardiac frequency bandpass filter further comprises processing time samples of each pixel in the angiographic images as a separate signal, and applying the cardiac frequency bandpass filter to the pixel-wise signals.

In accordance with another aspect, a contemporaneously measured cardiac signal is obtained and the contemporaneously measured cardiac signal is used as a cross correlation target to provide a bandpass cardiac frequency filter limited in range by the frequency of the measured cardiac signal.

In accordance with another aspect, the cardiac frequency band pass filter comprises one of a real valued filter that is rendered in image form using grayscale, or a complex valued filter that is rendered in image form based on a cardiac frequency magnitude and a cardiac frequency phase.

In accordance with another aspect, applying the Eulerian magnification comprises applying a spatial decomposition to a sequence of angiographic images, applying a temporal filter to the spatially decomposed sequence of angiographic images, selectively magnifying one or more of the dual spatially decomposed and temporally filtered sequence of angiographic images, and reassembling the selectively magnified sequence of angiographic images with the sequence of angiographic images into a combined sequence of angiographic images to allow visualization of an amplified spatiotemporal reconstruction.

In accordance with another aspect, applying the spatial decomposition further comprises performing multiscale anisotropic filtering or applying a spatial transformation comprising one of shearlets or ridgelets.

In accordance with another aspect, angiographic images with temporal and spatial phenomena of interest are selected, including temporal phenomena corresponding to a cardiac frequency band.

In accordance with another aspect, applying the spatial decomposition comprises performing a spatial decomposition of an angiographic image into several images each with different spatial characteristics, including filtering for spatial structures of specific spatial frequencies.

In accordance with another aspect, the cardiac frequency bandpass filter is applied with a value of zero for temporal phenomena outside of the cardiac frequency band, and angiographic images are reconstructed including the cardiac frequency phenomena with magnified spatial translations.

Still other objects and advantages of these techniques will be apparent from the specification and drawings.

BRIEF DESCRIPTION OF THE DRAWINGS

The drawings illustrate preferred embodiments presently contemplated for carrying out aspects of the invention. In the drawings.

DETAILED DESCRIPTION

Methods, systems and computer readable media for reconstructing cardiac frequency phenomena in angiographic data that do not rely on wavelets for spatiotemporal reconstruction are provided. A sequence of angiographic images (i.e., two dimensional projection images) is acquired at faster than cardiac rate and processed to provide a spatiotemporal reconstruction of moving vascular pulse waves. To generate the spatiotemporal reconstruction of moving vascular pulse waves, a cardiac frequency bandpass filter may be applied to the angiographic data, in some aspects with Eulerian magnification and amplification, to generate a spatiotemporal reconstruction of cardiac frequency angiographic phenomena. These techniques are described in additional detail below.

Referring to FIGS. 1-4, exemplary systems or devices that may be employed for carrying out embodiments of the invention are illustrated. It is understood that such systems and devices are only exemplary of representative systems and devices and that other hardware and software configurations are suitable for use with present techniques. Thus, present techniques are not intended to be limited to the specific systems and devices illustrated herein, and it is recognized that other suitable systems and devices can be employed without departing from the spirit and scope of the subject matter provided herein.

For reconstructing a moving vascular pulse wave, raw data is acquired via a fluoroscopic angiogram imaging system at a rate higher than cardiac frequency (e.g., images may be acquired at a rate up to 30 Hz). In aspects, and according to the Nyqvist Sampling Theorem, images are acquired by the system at over twice as fast as the highest frequency component of the cardiac signal. Given an angiogram obtained at faster than cardiac rate, the images may be processed according to the techniques provided herein to generate a time varying spatial reconstruction of the cardiac frequency angiographic phenomena.

Figure 1A:
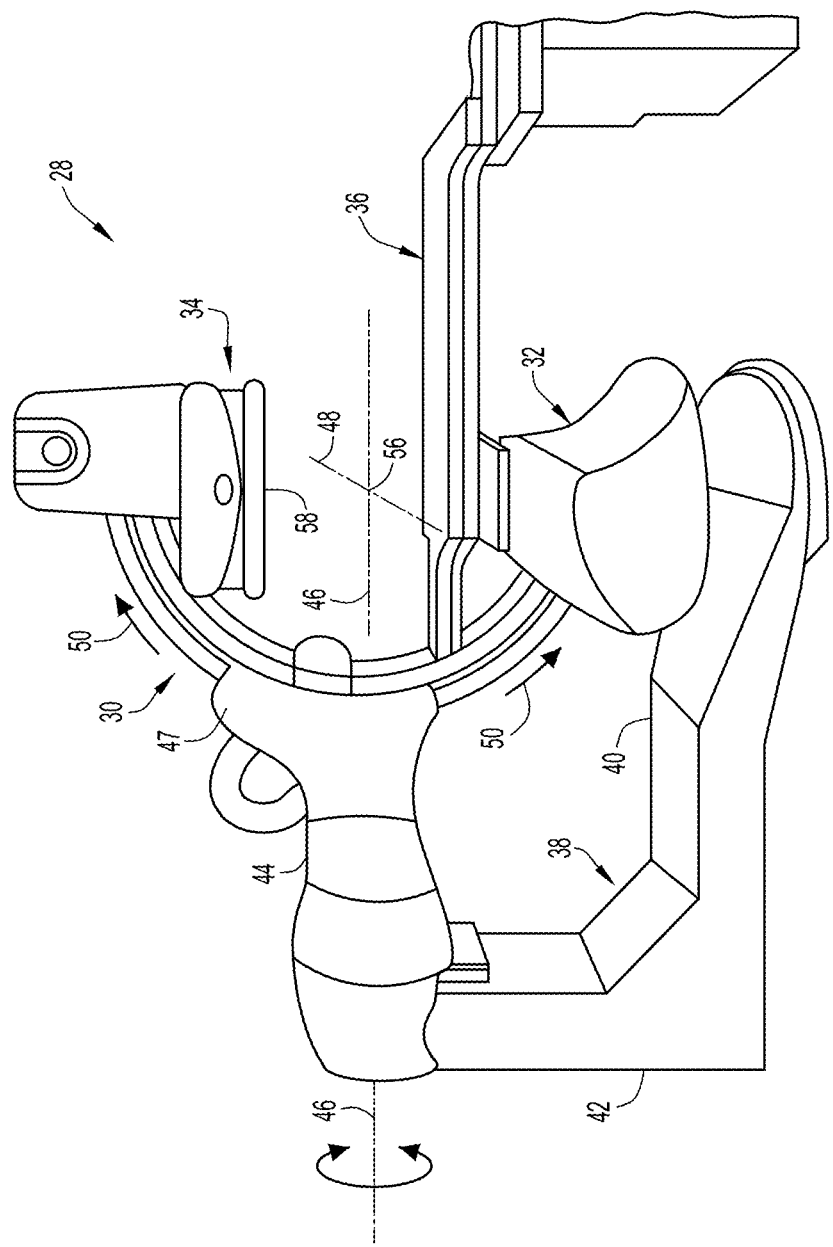
FIGS. 1A and 1B illustrate a rotational x-ray system that may be used with aspects of the disclosure for acquiring angiographic data.
Figure 1B:
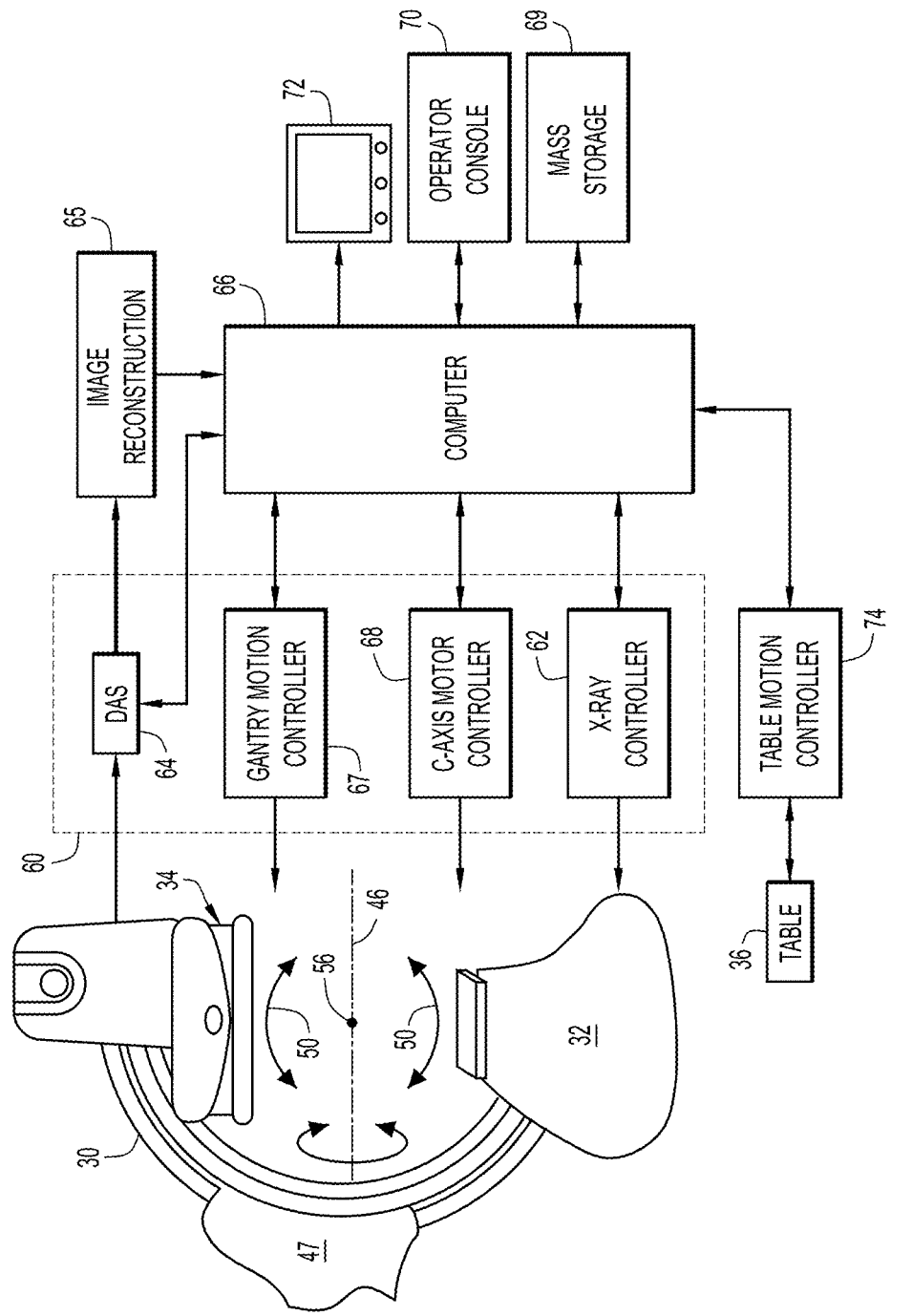

Referring first to FIGS. 1A and 1B, a rotational x-ray system 28 is illustrated that may be employed for obtaining an angiogram at faster than cardiac rate, such as via fluoroscopic angiography. As previously described, in acquiring an angiogram, a chemical contrast agent is injected into the patient positioned between an x-ray source and detector, and x-ray projections are captured by the x-ray detector as a two-dimensional image. A sequence of two dimensional projection images comprises an angiographic study, with the angiographic image frames acquired at faster than cardiac frequency to allow spatiotemporal reconstruction of the cardiac frequency phenomena into a cardiac space angiogram.

As shown in FIG. 1A, an example of an angiogram imaging system is shown in the form of a rotational x-ray system 28 including a gantry having a C-arm 30 which carries an x-ray source assembly 32 on one of its ends and an x-ray detector array assembly 34 at its other end. The gantry enables the x-ray source 32 and detector 34 to be oriented in different positions and angles around a patient disposed on a table 36, while providing to a physician access to the patient. The gantry includes a pedestal 38 which has a horizontal leg 40 that extends beneath the table 36 and a vertical leg 42 that extends upward at the end of the horizontal leg 40 that is spaced apart from table 36. A support arm 44 is rotatably fastened to the upper end of vertical leg 42 for rotation about a horizontal pivot axis 46.

The pivot axis 46 is aligned with the centerline of the table 36, and the arm 44 extends radially outward from the pivot axis 46 to support a C-arm drive assembly 47 on its outer end. The C-arm 30 is slidably fastened to the drive assembly 47 and is coupled to a drive motor (not shown) which slides the C-arm 30 to revolve about a C-axis 48 as indicated by arrows 50. The pivot axis 46 and C-axis 48 intersect each other, at an isocenter 56 located above the table 36, and are perpendicular to each other.

The x-ray source assembly 32 is mounted to one end of the C-arm 30 and the detector array assembly 34 is mounted to its other end. The x-ray source assembly 32 emits a beam of x-rays which are directed at the detector array assembly 34. Both assemblies 32 and 34 extend radially inward to the pivot axis 46 such that the center ray of this beam passes through the system isocenter 56. The center ray of the beam thus can be rotated about the system isocenter around either the pivot axis 46 or the C-axis 48, or both, during the acquisition of x-ray attenuation data from a subject placed on the table 36.

The x-ray source assembly 32 contains an x-ray source which emits a beam of x-rays when energized. The center ray passes through the system isocenter 56 and impinges on a two-dimensional flat panel digital detector 58 housed in the detector assembly 34. The detector 58 may be, for example, a 2048×2048 element two-dimensional array of detector elements. Each element produces an electrical signal that represents the intensity of an impinging x-ray and hence the attenuation of the x-ray as it passes through the patient. During a scan, the x-ray source assembly 32 and detector array assembly 34 are rotated about the system isocenter 56 to acquire x-ray attenuation projection data from different angles. In some aspects, the detector array is able to acquire 50 projections, or views, per second which is the limiting factor that determines how many views can be acquired for a prescribed scan path and speed.

Referring to FIG. 1B, the rotation of the assemblies 32 and 34 and the operation of the x-ray source are governed by a control mechanism 60 of the x-ray system. The control mechanism 60 includes an x-ray controller 62 that provides power and timing signals to the x-ray source 52. A data acquisition system (DAS) 64 in the control mechanism 60 samples data from detector elements and passes the data to an image reconstructor 65. The image reconstructor 65 receives digitized x-ray data from the DAS 64 and performs high speed image reconstruction according to the methods of the present disclosure. The reconstructed image is applied as an input to a computer 66 which stores the image in a mass storage device 69 or processes the image further.

The control mechanism 60 also includes gantry motor controller 67 and a C-axis motor controller 68. In response to motion commands from the computer 66, the motor controllers 67 and 68 provide power to motors in the x-ray system that produce the rotations about respective pivot axis 46 and C-axis 48. The computer 66 also receives commands and scanning parameters from an operator via console 70 that has a keyboard and other manually operable controls. An associated display 72 allows the operator to observe the reconstructed image and other data from the computer 66. The operator supplied commands are used by the computer 66 under the direction of stored programs to provide control signals and information to the DAS 64, the x-ray controller 62 and the motor controllers 67 and 68. In addition, computer 66 operates a table motor controller 74 which controls the motorized table 36 to position the patient with respect to the system isocenter 56.

Figure 2:
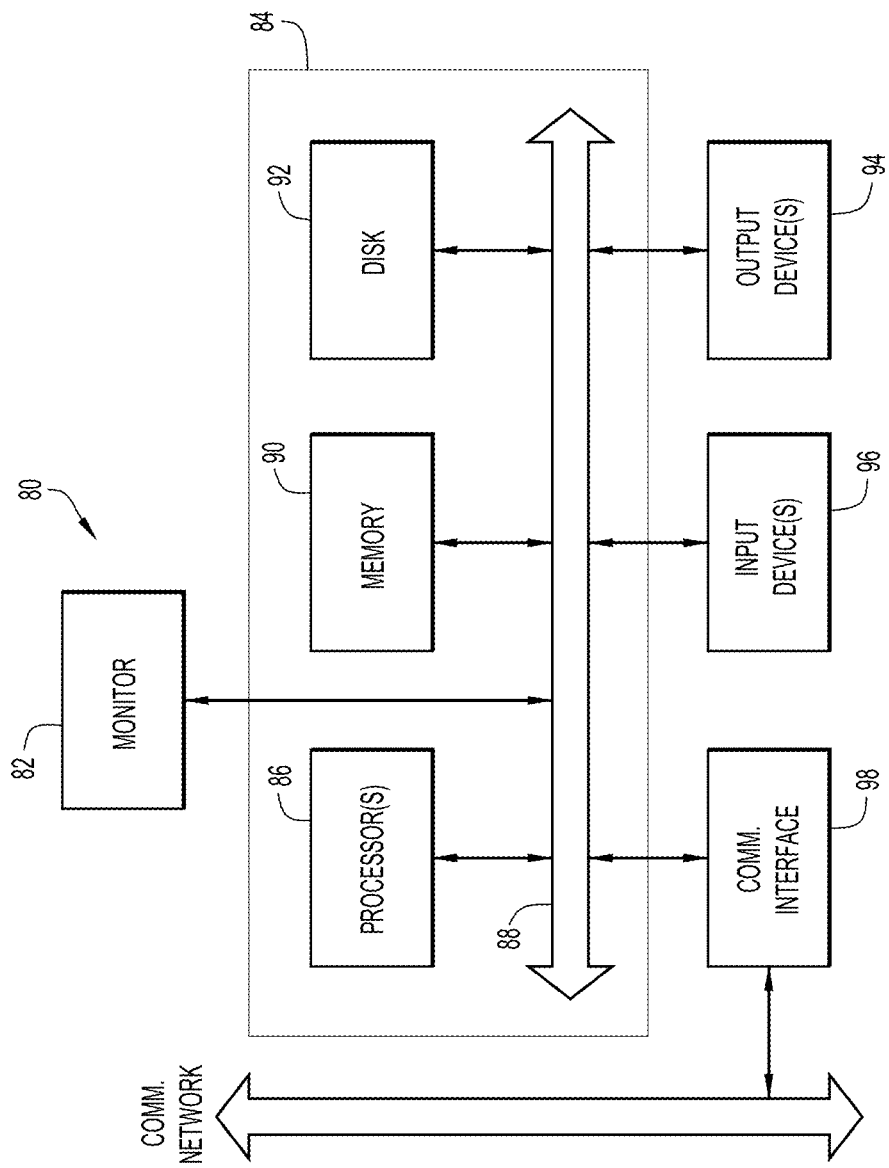
FIG. 2 is a block diagram of a computer system or information processing device that may be used with aspects of the disclosure.

Referring now to FIG. 2, a block diagram of a computer system or information processing device 80 (e.g., computer 66 in FIG. 1B) is illustrated that may be incorporated into an angiographic imaging system, such as the rotational x-ray system 28 of FIGS. 1A and 1B, to provide enhanced functionality or used as a standalone device for the extraction of cardiac frequency phenomena from angiographic data according to an embodiment of the present invention. In one embodiment, computer system 80 includes monitor or display 82, computer 84 (which includes processor(s) 86, bus subsystem 88, memory subsystem 90, and disk subsystem 92), user output devices 94, user input devices 96, and communications interface 98. Monitor 82 can include hardware and/or software elements configured to generate visual representations or displays of information. Some examples of monitor 82 may include familiar display devices, such as a television monitor, a cathode ray tube (CRT), a liquid crystal display (LCD), or the like. In some embodiments, monitor 82 may provide an input interface, such as incorporating touch screen technologies.

Computer 84 can include familiar computer components, such as one or more central processing units (CPUs), memories or storage devices, graphics processing units (GPUs), communication systems, interface cards, or the like. As shown in FIG. 2, computer 84 may include one or more processor(s) 86 that communicate with a number of peripheral devices via bus subsystem 88. Processor(s) 86 may include commercially available central processing units or the like. Bus subsystem 88 can include mechanisms for letting the various components and subsystems of computer 84 communicate with each other as intended. Although bus subsystem 88 is shown schematically as a single bus, alternative embodiments of the bus subsystem may utilize multiple bus subsystems. Peripheral devices that communicate with processor(s) 86 may include memory subsystem 90, disk subsystem 92, user output devices 94, user input devices 96, communications interface 98, or the like.

Memory subsystem 90 and disk subsystem 92 are examples of physical storage media configured to store data. Memory subsystem 90 may include a number of memories including random access memory (RAM) for volatile storage of program code, instructions, and data during program execution and read only memory (ROM) in which fixed program code, instructions, and data are stored. Disk subsystem 92 may include a number of file storage systems providing persistent (non-volatile) storage for programs and data. Other types of physical storage media include floppy disks, removable hard disks, optical storage media such as CD-ROMs, DVDs and bar codes, semiconductor memories such as flash memories, read-only-memories (ROMS), battery-backed volatile memories, networked storage devices, or the like. Memory subsystem 90 and disk subsystem 92 may be configured to store programming and data constructs that provide functionality or features of techniques discussed herein. Software code modules and/or processor instructions that when executed by processor(s) 86 implement or otherwise provide the functionality may be stored in memory subsystem 90 and disk subsystem 92.

User input devices 94 can include hardware and/or software elements configured to receive input from a user for processing by components of computer system 80. User input devices can include all possible types of devices and mechanisms for inputting information to computer system 84. These may include a keyboard, a keypad, a touch screen, a touch interface incorporated into a display, audio input devices such as microphones and voice recognition systems, and other types of input devices. In various embodiments, user input devices 94 can be embodied as a computer mouse, a trackball, a track pad, a joystick, a wireless remote, a drawing tablet, a voice command system, an eye tracking system, or the like. In some embodiments, user input devices 94 are configured to allow a user to select or otherwise interact with objects, icons, text, or the like that may appear on monitor 82 via a command, motions, or gestures, such as a click of a button or the like.

User output devices 96 can include hardware and/or software elements configured to output information to a user from components of computer system 80. User output devices can include all possible types of devices and mechanisms for outputting information from computer 84. These may include a display (e.g., monitor 82), a printer, a touch or force-feedback device, audio output devices, or the like.

Communications interface 98 can include hardware and/or software elements configured to provide unidirectional or bidirectional communication with other devices. For example, communications interface 98 may provide an interface between computer 84 and other communication networks and devices, such as via an internet connection.

Figure 3:
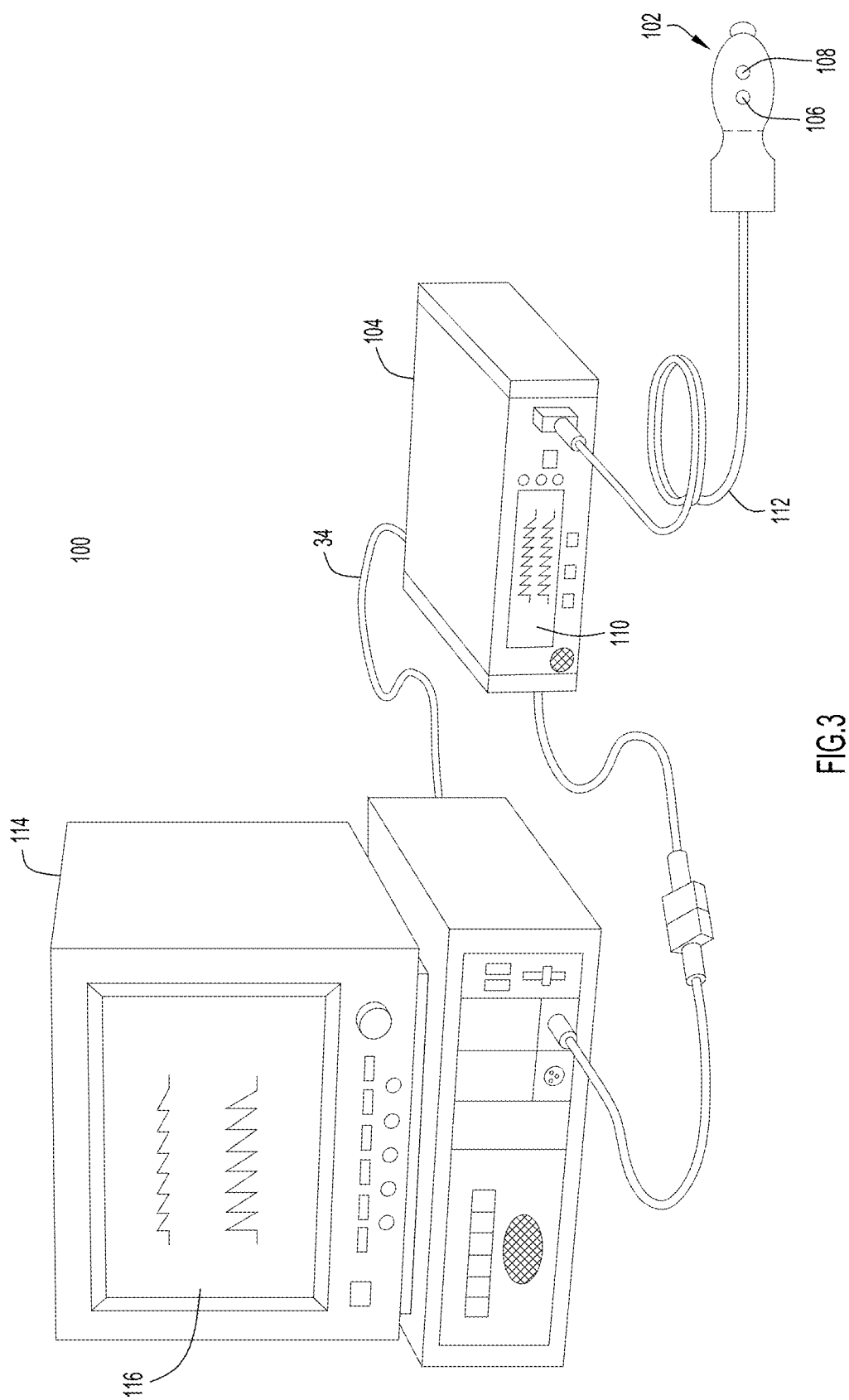
FIG. 3 is a perspective view of a pulse oximeter coupled to a multi-parameter patient monitor and a sensor that may be used with aspects of the disclosure for acquiring a cardiac signal.
Figure 4:
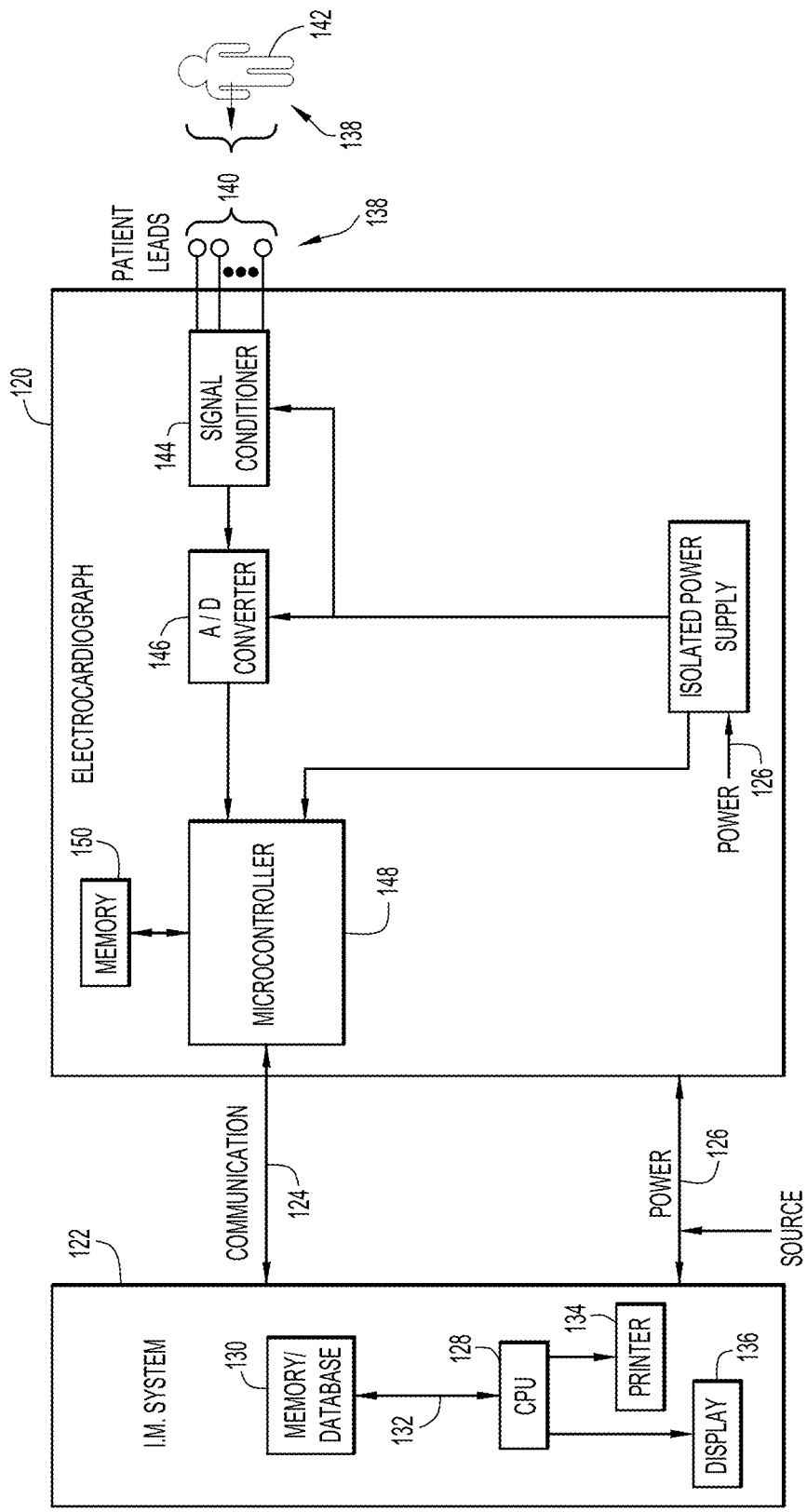
FIG. 4 is a block diagram of an electrocardiogram (EKG) device that may be used with aspects of the disclosure for acquiring a cardiac signal.

According to embodiments of the invention, it is recognized that, in addition to acquiring angiographic images, additional cardiac signals/data may be contemporaneously acquired to serve as a cross correlation target, for purposes of performing the spatiotemporal reconstruction of the vascular pulse waves based on the techniques provided herein. For example, the cardiac signals/data may serve as a reference cardiac signal for phase indexing pixels in the angiographic projections. FIGS. 3 and 4 illustrate exemplary devices for acquiring/providing a reference cardiac signal with such devices/systems in the form of a pulse oximetry system and/or an echocardiogram (EKG) system or device.

FIG. 3 is a perspective view of an example of a suitable pulse oximetry system 100 that includes a sensor 102 and a pulse oximetry monitor 104. The sensor 102 includes an emitter 106 for emitting light at certain wavelengths into a patient's tissue and a detector 108 for detecting the light after it is reflected and/or absorbed by the patient's tissue. The monitor 104 may be capable of calculating physiological characteristics received from the sensor 102 relating to light emission and detection. Further, the monitor 104 includes a display 110 capable of displaying the physiological characteristics and/or other information about the system. The sensor 102 is shown communicatively coupled to the monitor 104 via a cable 112, but alternatively may be communicatively coupled via a wireless transmission device or the like. In the illustrated embodiment the pulse oximetry system 100 also includes a multi-parameter patient monitor 114. In addition to the monitor 104, or alternatively, the multi-parameter patient monitor 114 may be capable of calculating physiological characteristics and providing a central display 116 for information from the monitor 104 and from other medical monitoring devices or systems. For example, the multi-parameter patient monitor 114 may display a patient's $SpO_2$ and pulse rate information from the monitor 104 and blood pressure from a blood pressure monitor on the display 116. In another embodiment, computer system 80 may be configured to include hardware and software for communicating with a pulse oximetry sensor, such as the sensor 102 shown in FIG. 3, as well as hardware and software to calculate physiological characteristics received from the pulse oximetry sensor and utilize such characteristics to extract cardiac frequency phenomena, and display the same, in accordance with the techniques described herein.

FIG. 4 is a schematic diagram of an electrocardiogram ("EKG") device 120 shown optionally connected to an information management system 122 through a communications link 124. A commonly used device for acquiring an EKG is a 12-lead electrocardiograph. The EKG device 120 and the information management system 122 receives power 126 from an external source. Among other things, the information management system 122 includes a central processing unit 128 connected to a memory unit, or database 130, via a data link 132. The CPU 128 processes data and is connected to an output, such as printer 134 and/or display 136. Alternatively, the electrocardiogram (EKG) device 120 can be connected directly to a printer 134 or display 136 through communications link 124, if the optional information management system 122 is not utilized. The software program according to embodiments provided herein may reside in either the EKG device 120, the information management system 122, or another device associated to receive signals from the EKG device 120. The EKG device 120 is connected to a plurality of patient lead wires 138, each having an electrode 140 to receive EKG signals from a patient 142 in a known manner. The EKG device 120 has a signal conditioner 144 that receives the EKG signals and filters noise, sets thresholds, segregates signals, and provides the appropriate number of EKG signals for the number of leads 138 to an A/D converter 146 which converts the analog signals to digital signals for processing by a microcontroller 148, or any other type of processing unit. Microcontroller 148 is connected to a memory unit 150, similar to memory unit 130, or any other computer readable storage medium. In another embodiment, computer system 80 may be configured to include hardware and software for communicating with EKG electrodes, such as electrodes 140 shown in FIG. 4, as well as hardware and software to calculate physiological characteristics received from the electrodes and utilize such characteristics to extract cardiac frequency phenomena, and display the same, in accordance with the techniques described herein.

As previously indicated, present embodiments are directed to systems, methods, and computer readable media for reconstructing cardiac frequency phenomena in angiographic data. A sequence of angiographic images (i.e., two dimensional projection images) is acquired at faster than cardiac rate (such as via the system of FIG. 1A, 1B) and analyzed (such as via the system of FIG. 2) to provide a spatiotemporal reconstruction (e.g., as described in the '761 patent) of moving vascular pulse waves utilizing the bandpass filtering and amplification techniques provided herein.

In some aspects, the spatiotemporal reconstructions are complex valued data of the same dimensionality as the projection, and each pixel at each time point has a complex valued datum. It may be represented as a real number and an imaginary number. For physiological interpretation, however, it is represented in polar form with magnitude and a phase. In aspects, the magnitude represents the variation of contrast in a given pixel at cardiac frequency, and the phase represents the phase relative to the cardiac cycle.

While the '761 patent uses a wavelet transform for yielding a time varying extraction of the cardiac frequency angiographic phenomena (i.e., the wavelet transform being applied to each of the pixel-wise time signals of the angiogram), it will be appreciated that other methods could be utilized for yielding the time varying extraction of the cardiac frequency angiographic phenomena.

FIGS. 6-9 are flowcharts corresponding to operations of the techniques provided herein. It will be appreciated that the operations described herein may be implemented in an angiographic imaging system or a standalone computer system to improve angiographic image processing and display technologies. According to an embodiment, a cardiac frequency bandpass filter may be applied to the angiographic data taken at greater than cardiac frequency to output the spatiotemporal reconstruction of cardiac frequency angiographic phenomena (e.g., moving vascular pulse waves). To extract the cardiac frequency phenomena from a cine sequence of angiographic images, a cardiac frequency bandpass filter is applied to the angiogram. In aspects, a contemporaneously measured cardiac signal (such as acquired from the pulse oximetry system of FIG. 3 or the electrocardiogram device of FIG. 4) may serve as a reference cardiac signal for phase indexing.

Figure 6:
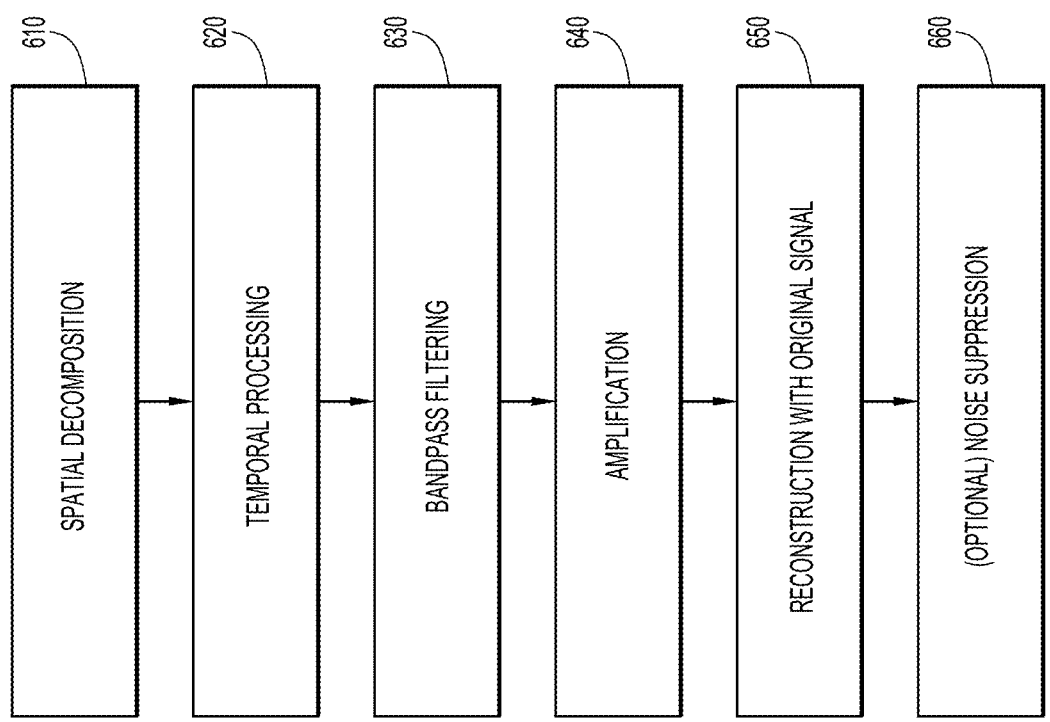
FIG. 6 shows a general approach for amplifying the spatiotemporal angiographic phenomena, according to aspects of the disclosure.

FIG. 6 shows a high level implementation of the techniques provided herein. While the operations are shown separately, it should be understood that certain operations (e.g., temporal processing, bandpass filtering, and amplification) may be combined and/or performed in a different order than as shown in this figure. At operation 610, the image is spatially decomposed. In an embodiment, the image may be decomposed into pixels, and subsequent computations performed pixel-wise. In other aspects, pixels may be grouped into different frequency bands, and computation may be performed band-wise.

Spatial decomposition is the separation of an image into several images each with different spatial characteristics. For example, images may be separated into groups corresponding to spatial structures of specific spatial frequencies. Examples of methods for generating a spatial decomposition include but are not limited to a Laplacian pyramid, a complex steerable pyramid, and a Reisz pyramid. In other aspects, spatial decomposition may include multiscale anisotropic filtering, or transformation based on shearlets or ridgelets. Any of these may be selected for extracting the cardiac frequency phenomena in a sequence of angiographic images, since cardiac frequency organization may occur in one or more specific scales of spatial structure. In aspects, the spatial frequency decomposition may be real-valued or complex-valued.

At operation 620, temporal processing may be performed to correlate observed intensities of pixels as a function of time to a translational motion signal. As the vascular pulse wave travels through the vascular system, temporal processing allows this translational motion signal to be extracted. At operation 630, the translational motion signal may be bandpass filtered, e.g., at cardiac frequency. In aspects, each pixel in an angiographic image may be treated as a separate signal as a function of time, and the cardiac frequency bandpass filter may be applied pixel-wise. In other aspects, the cardiac frequency bandpass filter may be applied to groups corresponding to spatial structures. In the limit, instead of a frequency bandpass filter, a contemporaneously measured cardiac signal (e.g., acquired from the pulse oximetry system of FIG. 3 or the electrocardiogram device of FIG. 4) may serve as a cross correlation target, furnishing a type of ultra-narrow bandpass cardiac frequency filter. In aspects, the contemporaneously measured cardiac signal serves as a reference cardiac signal for phase indexing.

At operation 640, the signal (e.g., extracted from the image using bandpass filtering, which corresponds to motion at cardiac scale) may undergo amplification. In aspects, amplification may be achieved by multiplying the signal by a constant. In other aspects, Eulerian magnification may be used. In some aspects, the amplification may be performed by isolating and then amplifying the cardiac frequency signal. In this case, the amplification signal may be recombined with the original signal, for example, by aligning the amplified signal with the original signal (e.g., based on time varying intensities, based on a timestamp, etc.). In some aspects, the amplified signal may be additively combined to the original signal. In other aspects, the amplified signal may be superimposed onto the original signal. Thus, at operation 650, the original signal may be combined or superimposed with the amplified bandpass signal to form a reconstructed signal. For example, Optionally, at operation 660, the reconstructed signal may undergo noise suppression (e.g., bilateral filtering or other suitable technique). These techniques provide a spatiotemporal reconstruction of cardiac frequency angiographic phenomena as output, shown as moving vascular pulse waves which may be amplified.

In other aspects, the cardiac frequency bandpass filter may be real valued or complex valued, according to embodiments. If the cardiac frequency bandpass filter is real valued, then the resulting cardiac frequency phenomena will be reevaluated, and may be rendered in image form using any suitable visualization format including grayscale, colorscale, and/or brightness. Alternately, if the cardiac frequency bandpass filter is complex valued, having a real component and an imaginary component, it may be represented in a polar form comprising a magnitude and a phase. After passage through a cardiac frequency bandpass filter, the magnitude may be interpreted as cardiac frequency magnitude, as in a "strength of the heart action." The phase may be interpreted as the temporal location within a cardiac cycle. The magnitude and the phase may be rendered using a brightness-hue color model, where the brightness of a pixel represents a cardiac frequency magnitude and the hue represents a cardiac frequency phase.

Figure 5:
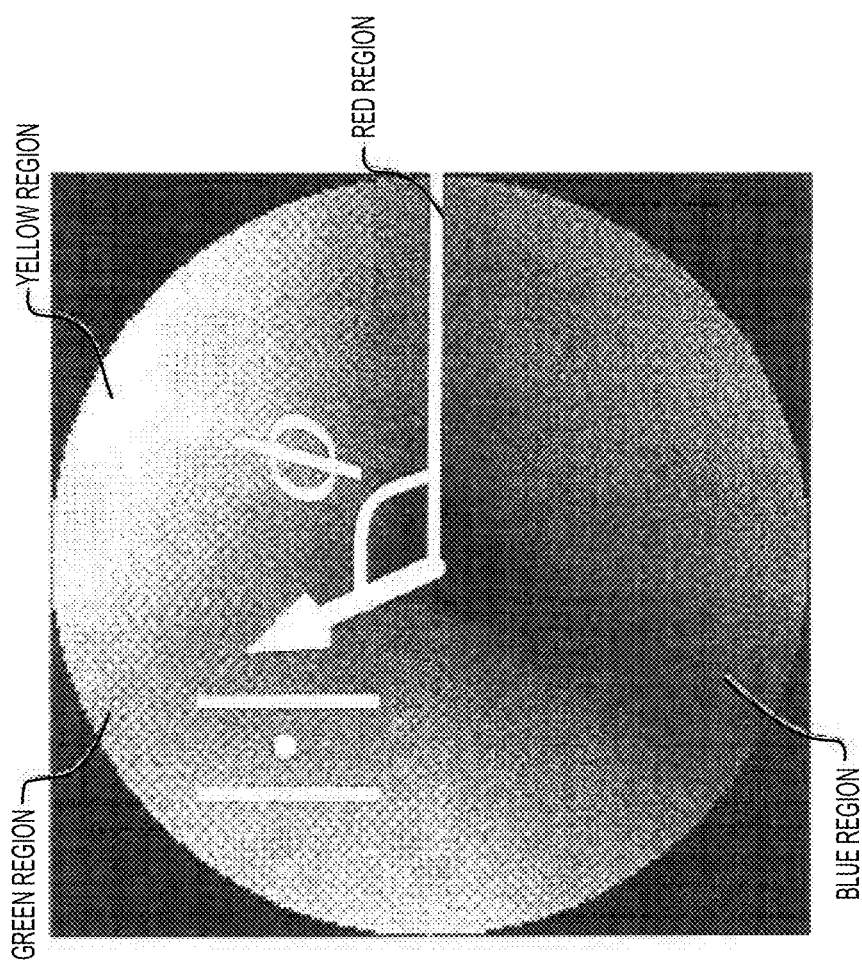
FIG. 5 illustrates a brightness hue color model for rendering a complex valued number according to aspects of the disclosure.

The cardiac frequency bandpass filter and amplified images may be rendered in gray scale or in a color scale (referring back to FIG. 5), where optionally color brightness may represent cardiac frequency magnitude or spatial motion speed, and color hue may represent cardiac frequency phase or spatial motion direction, depending on the user's choice of whether to emphasize the temporal or spatial properties in the cardiac frequency band of the reconstructed result. Although the image is submitted as grayscale, one of ordinary skill in the art would recognize that this grayscale image includes a spectrum of hues. The color model for rendering a complex valued number in a pixel is depicted in FIG. 5, and FIG. 5 may show a spectrum of color hues including a green region, a yellow region, a red region, and a blue region. A sequence of such images may be animated across the time indices to represent a cine video sequence of the motions of a train of vascular pulse waves, such as in the brain or heart or other vascular regions, for example.

Figure 7:
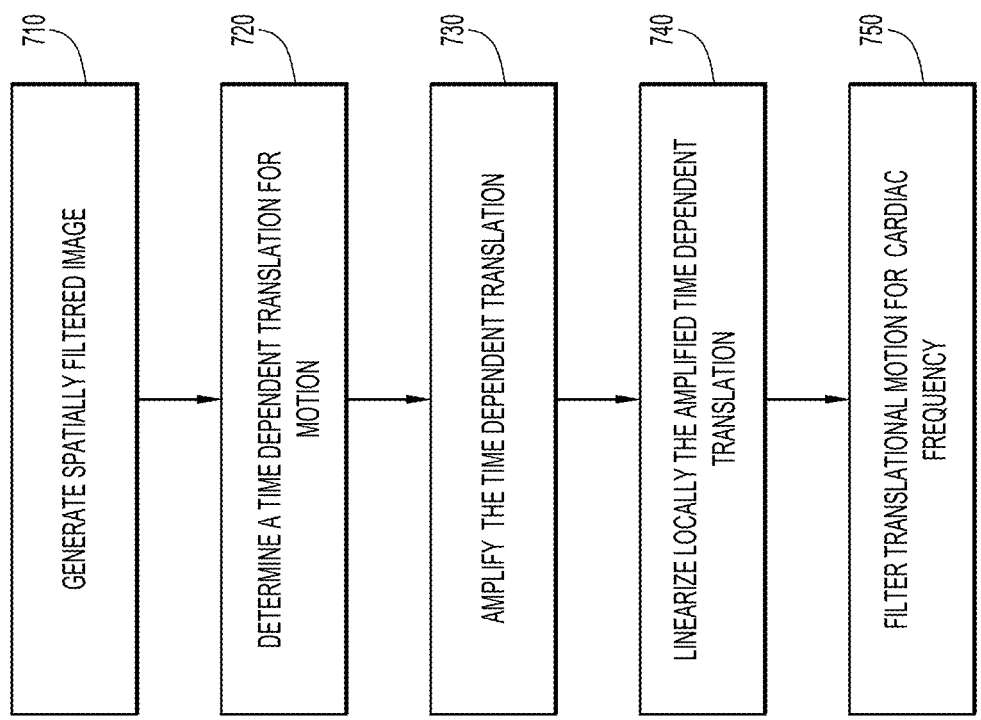
FIG. 7 is a detailed flowchart showing techniques for reconstructing cardiac frequency phenomena in angiographic data according to aspects of the disclosure.
Figure 8:
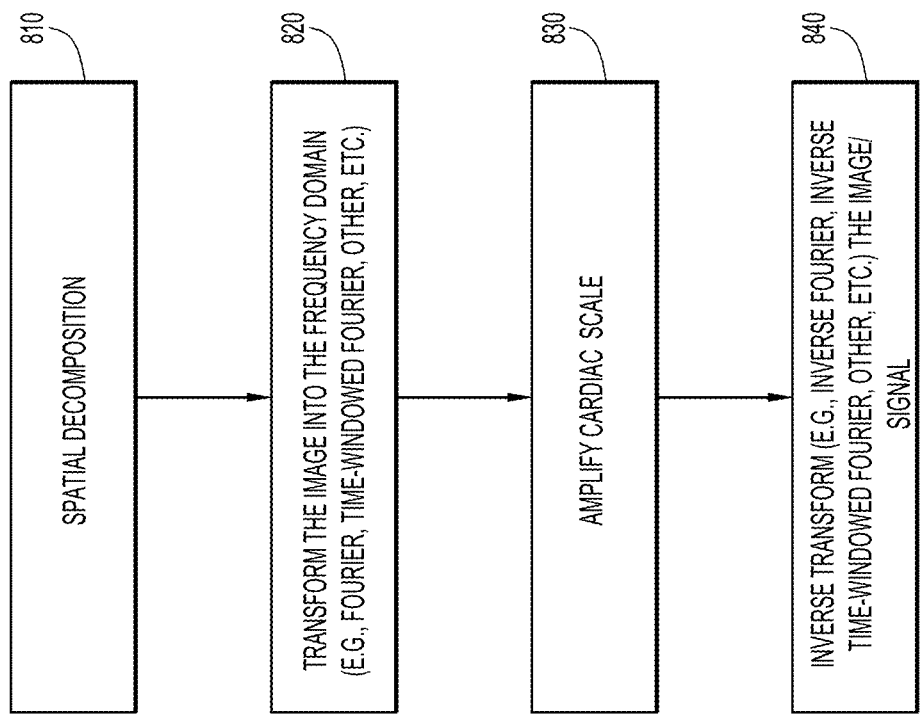
FIG. 8 shows a Fourier-based approach for amplifying the spatiotemporal angiographic phenomena, according to aspects of the disclosure.

With reference now to FIG. 7, an example is provided hereinbelow for a given spatially filtered image and for only one spatial dimension, x, and the time t dimension, t, for purposes of illustration. This representation corresponds to a continuous form of signals. However, it is understood that these continuous equations may be applied to process digitized images, according to techniques known in the art.

At operation 710, a spatially filtered image is generated. An image I(x,t) may undergo spatial decomposition, as provided herein. For example, spatial decomposition may include pyramidal decomposition, in which coarse filtering is used to separate regions into different frequency bands and fine filtering is used to refine the image. The spatially decomposed or spatially filtered image I(x,t) may be represented as:

$$f(x)=I(x,t)$$

At operation 720, a time-dependent translation (or temporal filter) is applied to x, to determine motion from vessels and extract cardiac frequency, wherein x is modified by a translation function $\partial(t)$ that is a function of t:

$$\hat{I}(x,t)=f(x+\partial(t))$$

At operation 730, the time-dependent translation to extract cardiac frequency motion is amplified by an amplification factor $\alpha$, which is applied to the translation function $\partial(t)$ to give:

$$\hat{I}(x,t)=f(x+(1+\alpha)\partial(t)).$$

In aspects, the term $f(x+\partial(t))$ is expanded as a first order Taylor expansion about x as:

$$\hat{I}(x,t)=f(x)+(1+\alpha)\partial(t)(\partial f(x)/\partial x)$$

In aspects, higher order terms (e.g., second order, third order, etc.) from the Taylor expansion may be included. This equation corresponds to the reconstructed signal including the amplified time dependent translation. For instance, the term $\partial(t) \partial f(x)/\partial x$ acts as a cardiac frequency bandpass filter (with time windowing) such that its value is zero for temporal phenomena outside of the cardiac frequency band. The time dependent translation is amplified by $(1+\alpha)$ (if a is chosen to be greater than zero) and combined with the original image f(x). This reconstruction may be shown as a cine video sequence to illustrate the spatiotemporal angiographic phenomena. Thus, by applying this strategy in combination with spatial decomposition, the images may be synthesized from their pyramids of spatially decomposed images. In aspects, amplification techniques may be optional, and only bandpass filtering may be performed.

In another aspect, a Fourier transform may act as a bandpass filter. At operation 810, a spatial decomposition is performed on the image. At operation 810, the image may be subjected to a cardiac scale bandpass filter and then pixel-wise transformed into the frequency domain using a Fourier transform. In other aspects, a time windowed Fourier transform may be applied. At operation 830, the cardiac scale may be amplified in the frequency domain. At operation 840, the amplified frequency domain image may be inverse transformed into the time domain, and the spatiotemporal angiographic phenomena with an amplified cardiac range may be displayed.

In another aspect, Eulerian magnification techniques may be modified and extended to allow for custom amplification of the cardiac angiographic phenomena. For example, present approaches extend these techniques to an angiogram, comprising a temporal sequence of images obtained during the passage of an intravascularly injected contrast bolus into the vasculature at faster than cardiac frequency. In this case, the amplification factor $\alpha$ may be selected to amplify spatiotemporal angiographic phenomenon, allowing for reproducibility by restricting and standardizing ranges for this factor. Additionally, Eulerian methods may select a bandpass filter for angiographic data, and may include higher order terms (e.g., second or third order terms as needed) to estimate the cardiac frequency band, which may be narrowly estimated and/or restricted from independent data such as a heartbeat monitor.

For example, amplification may be performed using Eulerian magnification methods. In this approach, a spatial filter is applied to a temporally arranged sequence of two or more images. A temporal filter is applied to the plurality of results of the spatial filter. One or more of the dual spatial and temporal filtered results are selectively amplified, and then reassembled into a sequence of images in order to yield an amplified effect corresponding to reconstruction of spatiotemporal phenomena. These techniques may be applied to angiographic images in order to select for those with temporal and spatial phenomena of interest, including temporal phenomena corresponding to the cardiac frequency phenomena.

According to an additional embodiment of the invention, shearlet or ridgelet transforms may be used in extracting cardiac frequency phenomena in angiographic data. Shearlet and ridgelet transforms accommodate multivariate functions that are governed by anisotropic features, such as edges in images. Wavelets, as isotropic objects, are not capable of capturing such phenomena. While wavelet transforms may be used for purposes of time-domain resolution, shearlet and ridgelet transforms may be used for spatial resolution, allowing a multi-resolution (e.g., 2D-spatial and temporal) analysis of the angiographic data to be performed.

Figure 9:
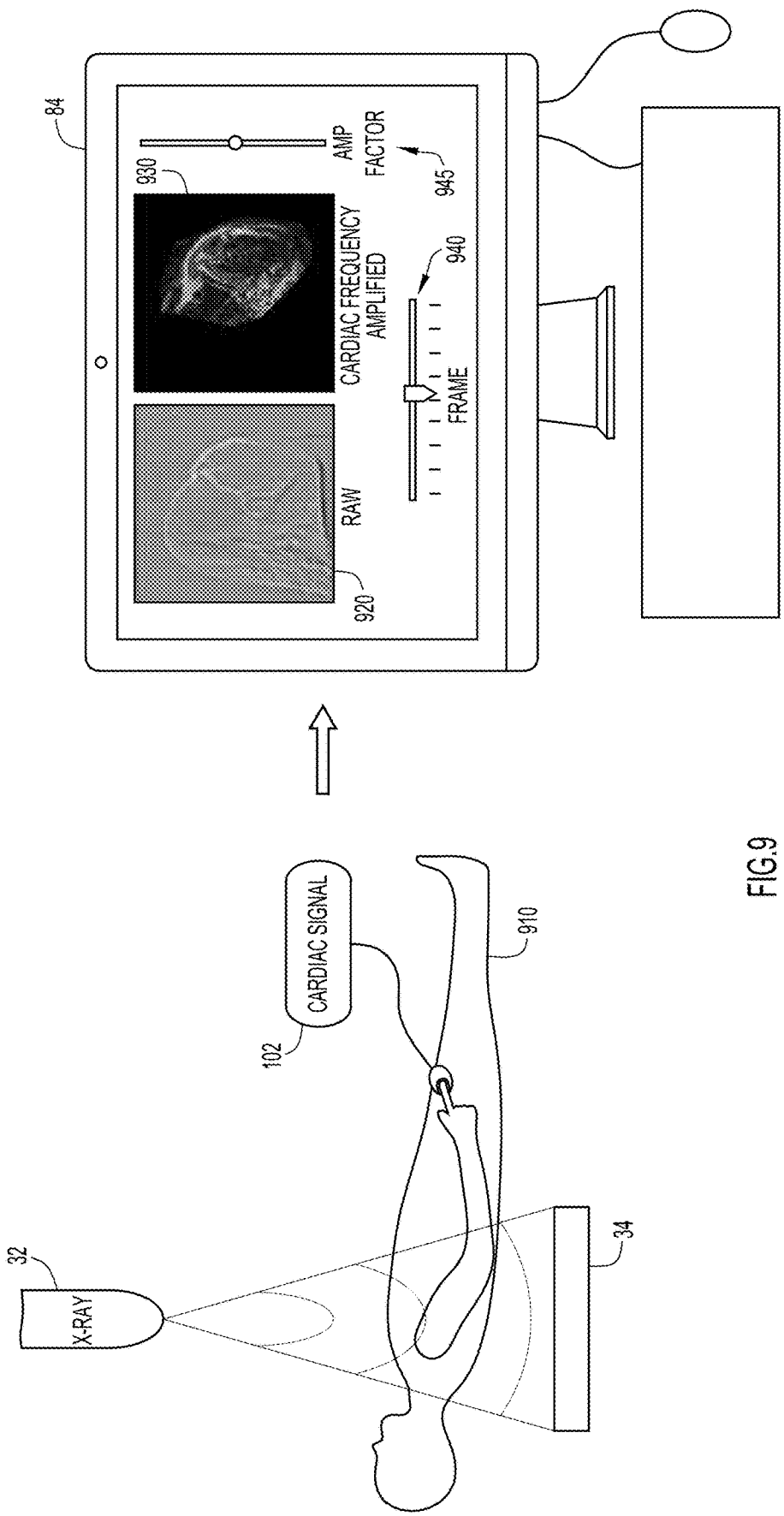
FIG. 9 shows an example implementation of reconstructing cardiac frequency phenomena according to aspects of the disclosure.

An example implementation is provided in FIG. 9. In this example, a bandpass filter is applied with an amplification factor to visualize the cardiac frequency phenomena. The left hand portion of the diagram shows a patient 910 undergoing an angiogram simultaneous with a cardiac signal being recorded from a finger pulse oximeter 102 (also known as optical plethysmogram).

The angiogram is obtained by injecting a bolus of contrast into the patient and acquiring angiographic images at faster than cardiac frequency. The cardiac frequency may be obtained from the patient's cardiac signal. In some aspects, the cardiac signal may vary as a function of time. In this case, the momentary cardiac signal may be referenced with respect to corresponding obtained images.

In this example, a graphical user interface is shown with two main display elements 920 and 930 and two visual control widgets 940 and 945. It will be appreciated that the graphical user interface could be displayed on a computer monitor, such as the monitor of computer system 80. The two main display elements are a cardiac angiogram image 920 without cardiac frequency amplification (left on the computer monitor, labeled "Raw") and a cardiac angiogram image 930 with cardiac frequency amplification (right on the computer monitor, labeled "Cardiac Frequency Amplified," with the brightness-hue model for cardiac frequency magnitude and phase). Other display methods including but not limited to grayscale, monochrome, etc. are contemplated for use with present techniques. In this example, a horizontally oriented slider control widget 940 (labeled "Frame"), positioned below the images, may be moved left and right on the screen by a user (e.g., by dragging with a mouse) to control the image frame being displayed. A cardiac frequency filter (as described in FIGS. 6-8) is applied to all image frames of the angiographic image sequence, and a clinician or radiologist may inspect one frame at a time. Optionally, a 3D rendering of the cardiac frequency-amplified image is provided, e.g., using the techniques described in co-pending U.S. patent application, Ser. No. 16/784,125 filed on Feb. 6, 2020, the contents of which are incorporated by reference herein in their entirety.

The graphical user interface also includes a vertically oriented slider control 945 on the right (labeled "Amp Factor") that can be adjusted by a user (e.g., by dragging with a mouse) to specify the degree of amplification of cardiac frequency. By controlling these parameters while viewing the images, users who are interpreting the images may modify the amplification and spatial resolution of the images based on the techniques provided herein, to customize these settings for specific medical analysis. These techniques may provide medical insight into cardiac frequency activity transpiring in the subject being imaged.

Figure 10:
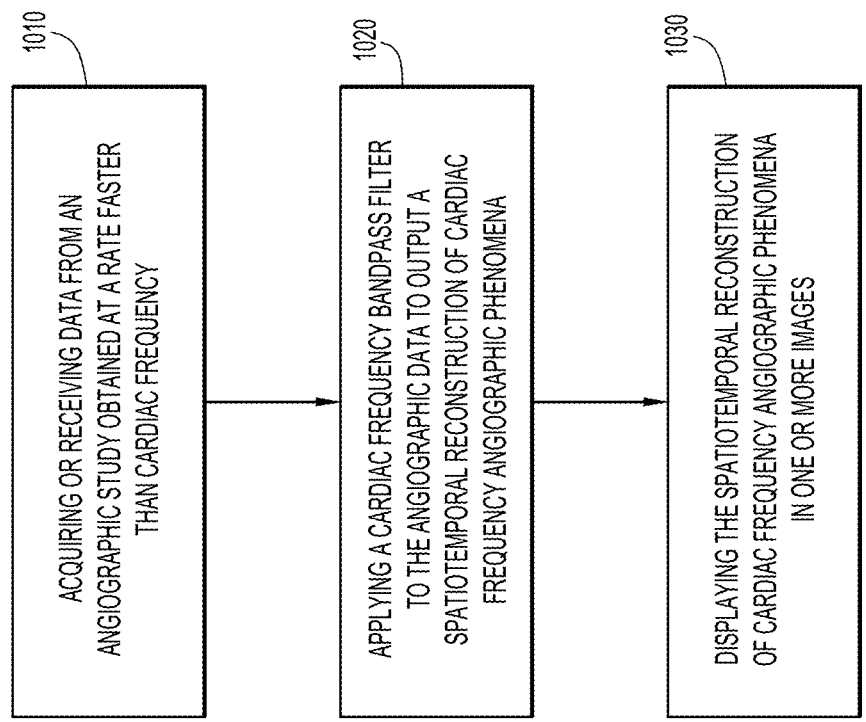
FIG. 10 shows a high level flowchart of techniques for reconstructing cardiac frequency phenomena in angiographic data according to aspects of the disclosure.

FIG. 10 shows high level operations of the techniques provided herein. At operation 1010, data is acquired or received from an angiographic study obtained at a rate faster than cardiac frequency. At operation 1020, a cardiac frequency bandpass filter is applied to the angiographic data to output a spatiotemporal reconstruction of cardiac frequency angiographic phenomena. At operation 1030, the spatiotemporal reconstruction of cardiac frequency angiographic phenomena in one or more images is displayed.

Beneficially, embodiments provided herein include a system, method, and computer readable media for spatiotemporally reconstructing cardiac frequency phenomena in angiographic data that apply a cardiac frequency bandpass filter to angiographic data, with or without a Eulerian magnification, for extracting and potentially magnifying cardiac frequency phenomena. In some aspects, these techniques may be combined with the techniques provided in the '761 patent to further magnify cardiac frequency phenomena.

These techniques may be applied with a hardware system designed to obtain angiographic images, and in particular an angiographic system, to obtain images for a patient. These techniques provide an improvement in the art over existing angiographic approaches, namely, allowing the spatiotemporal cardiac frequency phenomenon to be amplified an superimposed on the angiographic signal. This enhancement may allow improved visualization by amplification of vascular pulse waves as well as resolution of fine detail (based on spatial filtering techniques), as compared to existing techniques. In aspects, amplification may be custom controlled as described in herein to allow varying degrees of amplification and resolution, which may be customized to yield information for various medical analysis.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall there-between.

The techniques provided herein have been described in terms of the preferred embodiment, and it is recognized that equivalents, alternatives, and modifications, aside from those expressly stated, are possible and within the scope of the appending claims.

What is claimed is:

1. A method for extracting cardiac frequency angiographic phenomena from an angiographic study obtained at a rate faster than cardiac frequency, the method comprising:
    acquiring or receiving data from an angiographic study obtained at a rate faster than cardiac frequency;
    applying a cardiac frequency bandpass filter to the angiographic data to generate a spatiotemporal reconstruction of cardiac frequency angiographic phenomena; and
    displaying the spatiotemporal reconstruction of cardiac frequency angiographic phenomena in one or more images.

2. The method of claim 1, wherein applying the cardiac frequency bandpass filter extracts the cardiac frequency angiographic phenomena from a cine sequence of angiographic images.

3. The method of claim 1, wherein applying the cardiac frequency bandpass filter further comprises:
    processing time samples of each pixel in the angiographic images as a separate signal; and
    applying the cardiac frequency bandpass filter to the pixel-wise signals.

4. The method of claim 1, further comprising obtaining a contemporaneously measured cardiac signal and using the contemporaneously measured cardiac signal as a cross correlation target to provide a bandpass cardiac frequency filter limited in range by a frequency of the contemporaneously measured cardiac signal.

5. The method of claim 1, wherein the cardiac frequency bandpass filter comprises one of:
    a real valued filter that is rendered in image form using grayscale; or a complex valued filter that is rendered in image form based on a cardiac frequency magnitude and a cardiac frequency phase.

6. The method of claim 1, further comprising applying a Eulerian magnification to the angiographic data.

7. The method of claim 6, wherein applying the Eulerian magnification comprises:
    applying a spatial decomposition to a sequence of angiographic images;
    applying a temporal filter to the spatially decomposed sequence of angiographic images;
    selectively magnifying one or more of the dual spatially decomposed and temporally filtered sequence of angiographic images; and
    reassembling the selectively magnified sequence of angiographic images with the sequence of angiographic images into a combined sequence of angiographic images to allow visualization of an amplified spatiotemporal reconstruction.

8. The method of claim 7, wherein applying the spatial decomposition further comprises performing multiscale anisotropic filtering or applying a spatial transformation comprising one of shearlets or ridgelets.

9. The method of claim 7, further comprising selecting angiographic images with temporal and spatial phenomena of interest, including temporal phenomena corresponding to a cardiac frequency band.

10. The method of claim 7, wherein applying the spatial decomposition comprises performing a spatial decomposition of an angiographic image into several images each with different spatial characteristics, including filtering for spatial structures of specific spatial frequencies.

11. The method of claim 7, wherein the cardiac frequency bandpass filter is applied with a value of zero for temporal phenomena outside of a cardiac frequency band, and further comprising:
    reconstructing angiographic images including the cardiac frequency angiographic phenomena with magnified spatial translations.

12. The method of claim 11, wherein the reconstructed angiographic images are provided as a cine video sequence.

13. An angiographic system for extracting cardiac frequency angiographic phenomena obtained at a rate faster than cardiac frequency, the angiographic system comprising:
    an x-ray source and x-ray detector for obtaining angiographic data;
    one or more computer processors;
    one or more computer readable storage media; and
    program instructions stored on the one or more computer readable storage media for execution by at least one of the one or more computer processors, the program instructions comprising instructions to:
    acquire or receive data from an angiographic study obtained at a rate faster than cardiac frequency;
    apply a cardiac frequency bandpass filter to the angiographic data to generate a spatiotemporal reconstruction of cardiac frequency angiographic phenomena; and
    display the spatiotemporal reconstruction of cardiac frequency angiographic phenomena in one or more images.

14. The system of claim 13, wherein the program instructions further comprise instructions to apply the cardiac frequency bandpass filter to extract the cardiac frequency angiographic phenomena from a cine sequence of angiographic images.

15. The system of claim 13, wherein the program instructions further comprise instructions to:
    process time samples of each pixel in the angiographic images as a separate signal; and
    apply the cardiac frequency bandpass filter to the pixel-wise signals.

16. The system of claim 13, wherein the program instructions further comprise instructions to:
    use a contemporaneously measured cardiac signal as a cross correlation target to provide a bandpass cardiac frequency filter limited in range by the frequency of the measured cardiac signal.

17. The system of claim 13, wherein the cardiac frequency bandpass filter comprises one of a real valued filter that is rendered in image form using grayscale; or a complex valued filter that is rendered in image form based on a cardiac frequency magnitude and a cardiac frequency phase.

18. The system of claim 13, wherein the program instructions further comprise instructions to:
    apply a Eulerian magnification to the angiographic data.

19. The system of claim 18, wherein the program instructions further comprise instructions to:
    apply a spatial decomposition to a sequence of angiographic images;

apply a temporal filter to the spatially decomposed sequence of angiographic images; selectively magnify one or more of the dual spatially decomposed and temporally filtered sequence of angiographic images; and reassemble the selectively magnified sequence of angiographic images with the sequence of angiographic images into a combined sequence of angiographic images to allow visualization of an amplified spatiotemporal reconstruction.

20. The system of claim 19, wherein the program instructions further comprise instructions to perform multiscale anisotropic filtering or apply a spatial transformation using shearlets or ridgelets.

21. The system of claim 19, wherein the program instructions further comprise instructions to:

select angiographic images with temporal and spatial phenomena of interest, including temporal phenomena corresponding to a cardiac frequency band.

22. The system of claim 19, wherein the program instructions further comprise instructions to:

perform a spatial decomposition of an angiographic image into several images each with different spatial characteristics, including filtering for spatial structures of specific spatial frequencies.

23. The system of claim 19, wherein the cardiac frequency bandpass filter is applied with a value of zero for temporal phenomena outside of a cardiac frequency band, and wherein the program instructions further comprise instructions to:

reconstruct angiographic images including the cardiac frequency phenomena with magnified spatial translations.

24. A computer program product comprising one or more computer readable storage media collectively having program instructions embodied therewith, the program instructions executable by a computer to cause the computer to:

acquire or receive data from an angiographic study obtained at a rate faster than cardiac frequency;

apply a cardiac frequency bandpass filter to the angiographic data to generate a spatiotemporal reconstruction of cardiac frequency angiographic phenomena; and display the spatiotemporal reconstruction of cardiac frequency angiographic phenomena in one or more images.

25. The computer program product of claim 24, wherein the program instructions executable by the computer further cause the computer to apply a Eulerian magnification to the angiographic data.

* * * * *